US010105500B2

(12) United States Patent
Longest et al.

(10) Patent No.: US 10,105,500 B2
(45) Date of Patent: Oct. 23, 2018

(54) DRY POWDER INHALER (DPI) DESIGNS FOR PRODUCING AEROSOLS WITH HIGH FINE PARTICLE FRACTIONS

(71) Applicant: VIRGINIA COMMONWEALTH UNIVERSITY, Richmond, VA (US)

(72) Inventors: Phillip Worth Longest, Richmond, VA (US); Michael Hindle, Richmond, VA (US); Yoen-Ju Son, Richmond, VA (US); Srinivas Ravindra Babu Behara, Richmond, VA (US); Dale Farkas, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 810 days.

(21) Appl. No.: 14/399,317

(22) PCT Filed: Apr. 23, 2013

(86) PCT No.: PCT/US2013/037685
§ 371 (c)(1),
(2) Date: Nov. 6, 2014

(87) PCT Pub. No.: WO2013/169473
PCT Pub. Date: Nov. 14, 2013

(65) Prior Publication Data

US 2015/0107589 A1 Apr. 23, 2015

Related U.S. Application Data

(60) Provisional application No. 61/644,463, filed on May 9, 2012, provisional application No. 61/644,465, filed
(Continued)

(51) Int. Cl.
*A61M 15/00* (2006.01)
*A61M 11/00* (2006.01)
(Continued)

(52) U.S. Cl.
CPC ............ *A61M 11/003* (2014.02); *A61K 9/14* (2013.01); *A61K 31/137* (2013.01); *A61K 47/02* (2013.01);
(Continued)

(58) Field of Classification Search
CPC .. A61M 11/003; A61M 11/005; A61M 11/02; A61M 15/0021; A61M 15/0028;
(Continued)

(56) References Cited

U.S. PATENT DOCUMENTS 2,517,482 A 8/1950 Hall
5,724,959 A * 3/1998 McAughey ........... A61M 15/00 128/200.18
(Continued)

FOREIGN PATENT DOCUMENTS

WO 99/33505 A1 7/1999
WO 02/080884 A2 10/2002

*Primary Examiner* — Lynne Anderson
(74) *Attorney, Agent, or Firm* — W&C IP

(57) ABSTRACT

A dry powder inhaler (DPI) device has a flow passage with a three-dimensional (3D) rod array. The rod array includes multiple rows each having multiple unidirectional rods. The rows are spaced apart along a primary direction of air flow and are staggered. A viewing window to the capsule chamber allows viewing of the capsule's position within the chamber which provides visual feedback of inhalation flow rate to the user during inhalation. The capsule chamber may orient the capsule parallel to a primary direction of air flow or perpendicular to a primary direction of air flow and provide capsule motion in a plane which is perpendicular to the primary direction of air flow.

26 Claims, 10 Drawing Sheets

Related U.S. Application Data on May 9, 2012, provisional application No. 61/802,961, filed on Mar. 18, 2013.

(51) Int. Cl.

| | |
|---|---|
| *A61K 9/14* | (2006.01) |
| *A61K 31/137* | (2006.01) |
| *A61K 47/02* | (2006.01) |
| *A61K 47/10* | (2017.01) |
| *A61K 47/12* | (2006.01) |
| *A61M 11/02* | (2006.01) |

(52) U.S. Cl.
CPC .............. *A61K 47/10* (2013.01); *A61K 47/12* (2013.01); *A61M 11/005* (2013.01); *A61M 15/003* (2014.02); *A61M 15/0021* (2014.02); *A61M 15/0028* (2013.01); *A61M 15/0045* (2013.01); *A61M 15/0086* (2013.01); *A61M 11/02* (2013.01); *A61M 2202/0092* (2013.01); *A61M 2202/064* (2013.01); *A61M 2205/0238* (2013.01); *A61M 2205/583* (2013.01); *A61M 2206/10* (2013.01); *A61M 2209/02* (2013.01)

(58) Field of Classification Search
CPC ............ A61M 15/003; A61M 15/0045; A61M 15/0086; A61M 15/0088; A61M 15/02; A61M 2202/064; A61M 2205/582; A61M 2206/10

See application file for complete search history.

(56) References Cited

U.S. PATENT DOCUMENTS

| | | | |
|---|---|---|---|
| 6,065,472 A * | 5/2000 | Anderson | A61M 15/0045 128/200.18 |
| 6,655,381 B2 | 12/2003 | Keane et al. | |
| 6,990,974 B2 * | 1/2006 | Staniforth | A61M 15/0086 128/200.18 |
| 8,371,291 B2 * | 2/2013 | Haroutunian | A61M 15/0086 128/200.14 |
| 2004/0035412 A1 | 2/2004 | Staniforth et al. | |
| 2009/0090361 A1 * | 4/2009 | Gumaste | A61M 15/0085 128/203.15 |
| 2011/0094507 A1 | 4/2011 | Wachtel et al. | |

* cited by examiner

DRY POWDER INHALER (DPI) DESIGNS FOR PRODUCING AEROSOLS WITH HIGH FINE PARTICLE FRACTIONS

CROSS-REFERENCE TO RELATED APPLICATIONS

This application claims benefit of U.S. Provisional Patent Application Nos. 61/644,463 and 61/644,465, both filed May 9, 2012, and U.S. Provisional Patent Application No. 61/802,961, filed Mar. 18, 2013, the complete contents of which are hereby incorporated by reference.

BACKGROUND OF THE INVENTION

Field of the Invention

The invention generally relates to inhalation therapy. In particular, the invention provides methods and devices for improved dispersion and deagglomeration of dry powders and new formulations therefor.

Background of the Invention

Dry powder inhalers (DPIs) are most efficient at delivering medicines to the lungs when they form aerosols with large numbers of small particles. In conventional DPIs, particles smaller than approximately 5 µm are considered advantageous for efficient lung deposition (Finlay 2001; Newman 2009). For enhanced condensational growth (ECG) or excipient enhanced growth (EEG) delivery, particles with an aerodynamic diameter of approximately 1 µm and below (i.e., submicrometer) are required (Hindle and Longest 2010; Longest et al., 2012a).

The mass fraction of aerosol particles with aerodynamic diameters of 5 µm and below (or 1 µm and below) is quantified as the fine particle fraction; $FPF_{5\ \mu m}$ (or $FPF_{1\ \mu m}$). The mass median aerodynamic diameter (MMAD) is also used to quantify size, which is defined as the aerodynamic particle size at the 50th percentile of a cumulative mass distribution curve. Increasing the FPF and decreasing the MMAD of pharmaceutical aerosols are critical for improved DPI performance.

A significant disadvantage of particles smaller than 5 µm is that they are often cohesive, especially if micronization has been employed to produce the particles. It is recognized that particle cohesion increases with decreasing particle size. Conventionally, these particles are either agglomerated or blended with larger carrier particles to overcome difficulties in dispersing them in the currently used DPIs. Producing powder formulations that are capable of being dispersed with high efficiency (increasing FPF and decreasing MMAD) using commercially available or novel DPIs is critical to improve delivery to the lungs using the powder inhalation technique.

Current DPI systems deliver only approximately 5-40% of the inhaled aerosol to the lungs, with the remainder depositing in the mouth and throat (Delvadia et al., 2012b; Geller et al., 2011; Longest et al., 2012b; Newman and Busse 2002). Aerosols depositing in the extrathoracic airways increase side effects, increase dose variability, and wastes valuable medication.

SUMMARY OF THE INVENTION

The invention provides devices and methods that increase FPF and decrease MMAD of the emitted aerosol. The innovations may occur together in a composite device, but may also be used individually to improve the performance of existing devices.

The invention furthermore provides submicrometer combination particle DPI formulations that incorporate one or more drugs, one or more hygroscopic excipients, one or more dispersion agents and one or more surface active agents into a combination particle. The ratio of each component can be optimized to ensure maximized drug load, optimal dispersibility, and hygroscopic growth for an EEG application.

The invention provides a three-dimensional array of rods (referred to as a 3D rod array or a 3D array system) to increase aerosol dispersion. Previous devices seek to increase dispersion using designs such as constriction tubes, impaction surfaces, two-dimensional meshes, and high speed jets. However, a three-dimensional (3D) array of rods is capable of improved drug aerosol dispersion and creating higher FPFs compared with previous designs at either the same flow rate or same pressure drop.

The invention provides generation of a high fine particle aerosol using a 3D rod array for particle deaggregation with an external air pressure source. In a number of scenarios, sufficient flow cannot be generated by the patient to create a high quality aerosol. Examples include nasal delivery of the aerosol, delivery during mechanical ventilation, and delivery to children or infants. Both Fowler (U.S. Pat. No. 2,992,645; 1961, off patent) and Sievers et al. (US 2010/0269819 A1) have previously disclosed use of an external air source for generating powder aerosols. However, the quality and performance of these aerosols is low compared with the proposed high fine particle aerosols, the low quality aerosols resulting in significant device and extrathoracic drug deposition. We disclose the use of an external air source combined with the 3D rod array geometry in order to generate a high quality aerosol with drug aerosol MMAD ≤1.5 µm and low delivery system drug deposition losses.

The invention provides a method of providing capsule motion in a plane perpendicular to the airflow direction and driven by the Bernoulli effect. Existing DPI designs use spinning capsules or capsules aligned with the flow direction. In the proposed device, the primary axis of the capsule may be at 90° with the primary flow direction.

The invention provides use of an L-shaped capsule chamber that can increase emitted drug dose, increase aerosol dispersion (decreased MMAD), and provide visual feedback to the patient or medical professional with respect to achieving the correct inhalation flow rate.

The invention provides coating of the capsule (or drug containing unit), capsule chamber, and/or inhaler with low surface energy compounds to improve emitted dose.

The invention provides submicrometer combination particle DPI formulations which may incorporate a drug/medicament, a hygroscopic excipient, a dispersion agent and a surface active agent into a combination particle. As used herein, dispersion agent is treated as an equivalent term to 'dispersibility enhancer'. 'Surface active agent' is also treated as an equivalent term to 'surfactant'. The ratio of each component can be optimized to ensure maximize drug load, optimal dispersibility and the required hygroscopic growth for an EEG application.

DETAILED DESCRIPTION

Figures 1A, 1B, 1C, 1D, 1E:
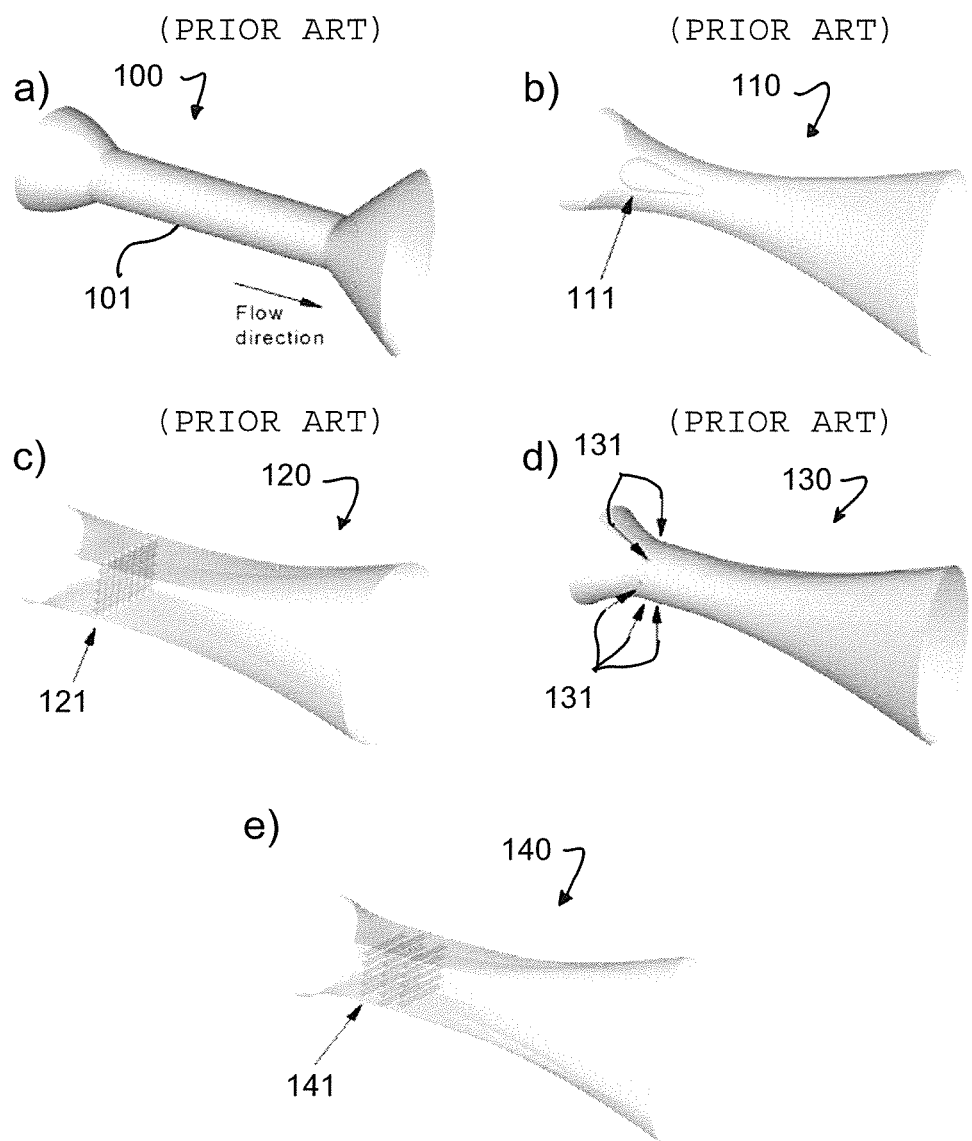
FIGS. 1a-1e. Flow passages designed to increase turbulence and improve the FPF and MMAD of an aerosol.

Referring now to the drawings, more specifically to FIGS. 1a to 1d, there are shown four existing embodiments of flow passages for dry particle inhalers. The flow passage 100 of a HandiHaler device (of small diameter or constricted tube 101) is shown in FIG. 1a. FIG. 1b shows a flow passage 110 with an internal impaction surface 111. FIG. 1c shows a flow passage 120 with a two-dimensional (2D) mesh 121. FIG. 1d shows a flow passage 130 with inward facing jets 131.

FIG. 1e shows an exemplary embodiment of a flow passage 140 comprising a 3D array of rods 141 according to the present invention. A three-dimensional (3D) array 141 of rods is generally capable of improved dispersion and creating higher FPFs compared with previous designs (such as those shown in FIGS. 1a-1d) at either the same flow rate or same pressure drop.

Figures 2A, 2B, 2C:
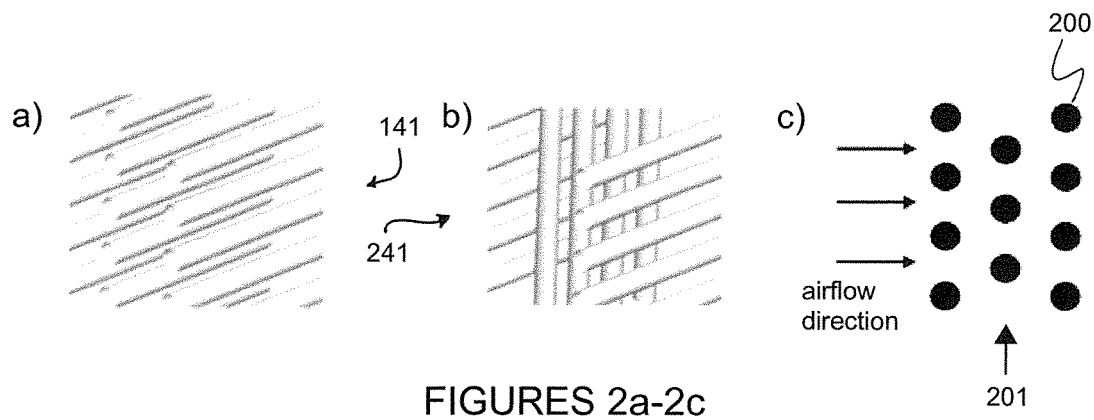
FIGS. 2a-2c. Close-up views of (a) a 3D rod array with parallel rows, (b) a 3D rod array with rows which are angled with respect to one another, and (c) cross-sectional view of the 3D rod array in the preferred embodiment with all rods in the same direction and the middle row staggered by 50%.

Generally, a 3D rod array 141 may be characterized by a plurality of rows each of which has a plurality of unidirectional rods disposed within a flow passage 140 of an inhaler and spaced apart along a primary direction of air flow in the flow passage. A primary direction of air flow in the flow passage may be described as a longitudinal direction or z-direction of the flow passage. Successive unidirectional rows in a primary direction of air flow may or may not lie on the same line and are preferably staggered. This generally means that the rods of a first row in a first x-y plane of the flow passage and the rods of a second row in a second x-y plane of the flow passage are not in direct alignment with each other in the z-direction. The rows are preferably parallel to one other, and the rods are generally parallel to one another. In a preferred embodiment the rods in the second x-y plane are offset by 1-99% (most preferably 50%) from the rods in the first x-y plane such that air flowing (generally with increased velocity) between two rods of the first row in the first plane impacts on one or more rods (preferably the centers of the rods) of the second row in the second plane. In a preferred embodiment, all the rods of the plurality of rows of a 3D rod array are oriented in a same direction. FIG. 2a illustrates a close-up view of a 3D rod array 141. FIG. 2c provides a cross-sectional view of a preferred embodiment of a 3D rod array wherein there are three rows of rods 200 and each successive row is offset by 50% from the preceding row such that air flowing between two rods impacts on the center of a rod in a subsequent row. Row 201 is shown 50% staggered with respect to an adjacent row.

The rods may have a circular cross-section, or cross-sections of other shapes such as oval, square, or rectangular. The rods may be fabricated from plastic or metal, such as stainless steel. The rods can be made from wire but are preferably not malleable. By this it is meant that the rods generally maintain their conformation, shapes, and relative positions. The use of metal instead of plastic rods may better maintain the integrity of the 3D rod array during flow and increases particle rebound, thereby further improving deaggregation of the aerosol and reducing MMAD.

Furthermore, the 3D array can be tuned by modifying the size of the rods, spacing within the array, pattern, and length of the array to modify or control system parameters such as pressure drop and level of particle dispersion. For example, the size of the rods may be reduced, for instance to a size in the range of 0.375 mm to 0.5 mm, to reduce the pressure drop of the air flow as it passes through the 3D rod array. In a preferred embodiment, the rods of each row have a uniform gap distance between adjacent rods and all rows are evenly spaced apart along a primary direction of air flow in the flow passage.

A 3D rod array may be incorporated into a drug delivery system including a unit configured to hold or support a dry powder, an aerosol delivery port, and a flow passage configured for air flow between the unit and the aerosol delivery port. The unit configured to hold a dry powder generally contains or supports the dry powder. Embodiments of the unit include a chamber which is configured to receive a capsule or blister containing a dry powder for inhalation or a capsule or blister itself, such as in a disposable inhaler produced such that one or more capsules or blisters are disposed within the device. Alternatively, the unit may be a surface which supports a pile of dry powder that is initially entrained by an airstream passing over the surface. The three-dimensional rod array may be disposed in the flow passage and comprise a plurality of rows, wherein each of said plurality of rows has a plurality of rods which are unidirectional, and wherein the rows are spaced apart along a primary direction of air flow in the flow passage. A 3D rod array may alternatively be incorporated into a complete DPI device having one or more air inlets, a capsule chamber associated with the one or more air inlets, an aerosol delivery port, and a flow passage configured for air flow between the capsule chamber and aerosol delivery port. In this description, the capsule and/or capsule chamber can be replaced with any drug containing element typically used in a DPI. These elements may include, but are not limited to a capsule, a blister, a film, a reservoir, a powder coated bead or body, a system of beads or bodies, powder containing element, or a dispensed amount of powder on a surface or in the air.

In some embodiments, a 3D rod array 241 may be characterized by multiple rows of unidirectional rods disposed within a flow passage 140 of an inhaler and spaced apart along a primary direction of air flow. The rows are preferably staggered such that increased velocity between two rods of one row impacts on a rod (e.g. the center of the rod) of a second row. Furthermore the rods of any one row are angled with respect to the rods of a neighboring row by an angle in between 0° and 180°, an exemplary angle being 90°, as shown in FIG. 2b.

In an embodiment, the invention provides generation of a high fine particle aerosol using a 3D rod array 141 for particle deaggregation combined with an external air pressure source. In a number of scenarios, sufficient flow cannot be generated by the patient to create a high quality aerosol. Examples include nasal delivery of the aerosol, delivery during mechanical ventilation, delivery to children or infants, and delivery to test animals. Both Fowler (U.S. Pat. No. 2,992,645; 1961, off patent) and Sievers et al. (US 2010/0269819 A1) have previously disclosed use of an external air source for generating powder aerosols, and FIG. 1d illustrates an embodiment of an air passage 130 with inlets for application of an external air source 131. However, the quality of aerosols associated with the prior art is low compared with the high fine particle aerosols which may be achieved in the practice of the invention, which generally results in significant device and extrathoracic drug deposition. An external air source (see FIG. 3) combined with the 3D rod array geometry 141 can generate a high quality aerosol with an MMAD ≤1.5 μm or ≤1 μm and low delivery system drug deposition losses.

A 3D array system may be used with capsule or blister-based inhalers, inhalers with powder reservoirs, inhalers with a film holding the drug, inhalers with the powder loaded on or in vibrating bodies, or other types of DPI devices. Powder formulations which may be used include a pure drug, a drug and carrier blend, and combination particles containing drug and excipient particles where the excipients are used to foster aerosol growth and dispersion. The formulation particle size can be submicrometer (<1 μm) or micrometer (≥1 μm) sized primary particles. Submicrometer combination formulations are preferable, however the DPI has also been shown to be suitable for the aerosolization of conventional micrometer sized formulations. The formulation primary particle size is determined using scanning electron microscopy (see, for example, FIGS. 14a-14c). The aerosol performance of the DPI is measured by the emitted aerosol MMAD and FPF. High efficiency aerosolization is demonstrated by low MMADs and high FPF's.

Figure 3:
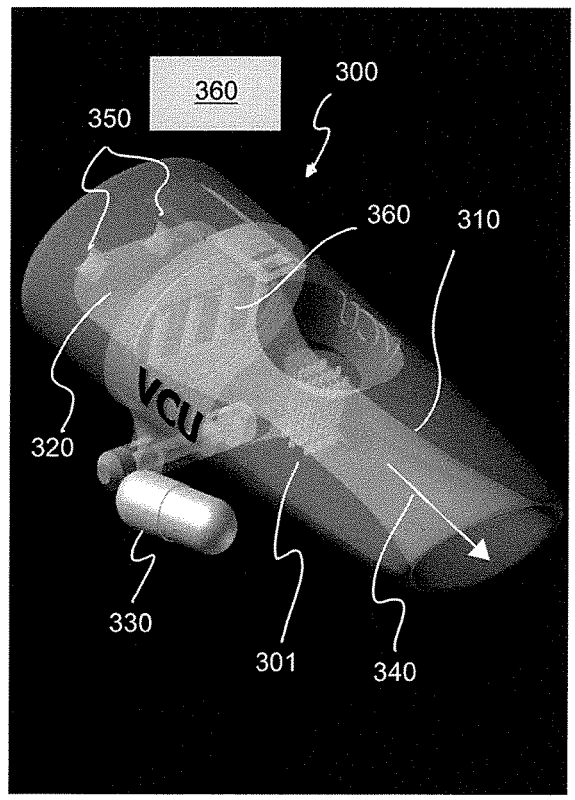
FIG. 3. Image of a $CC_1$-3D inhaler including a surface model of the composite device with an internal 3D rod array.

In another embodiment, the invention provides capsule motion in a plane which is perpendicular to a primary airflow direction, where the motion can be driven by the Bernoulli effect. A primary axis of the capsule is generally at a 90° angle with a primary flow direction. In FIG. 3 a DPI device 300 is shown which has a 3D rod array 301 disposed in a flow passage 310 which is adjoined to a capsule chamber 320 which orients a capsule 330 at a right angle to the direction of airflow 340 when the capsule is inserted into the capsule chamber. Two air inlets 350 allow for the ingress of air into the capsule chamber 320 and the flow passage 310. In some embodiments, an external air source 360 may be associated with one ore more air inlets of the device. Some embodiments may have one or more air inlets and/or one or more flow passages. Note that 'capsule chamber' may be referred to by other names in the art, such as 'capsule dispersion unit'. As used herein, both 'capsule chamber' and 'capsule dispersion unit' are functionally equivalent terms which may be used interchangeably. A capsule chamber 320 may be associated with a wire mesh, one or more bars 360, or other physical structure for preventing the ingress of the capsule into the flow passage 310. In some embodiments, a capsule 330 may be pierced prior to loading into capsule chamber 320, or alternatively, the capsule may be pre-pierced and having one or more apertures.

A capsule chamber may be configured such that alternating high velocity and high pressure (which may be characterized as the Bernoulli effect) on each side of the capsule causes rapid motion of the capsule back and forth (i.e. vibratory motion) in a direction or plane which is perpendicular to a primary direction of air flow in the capsule chamber. The motion may also be characterized as the capsule jiggling or bouncing within the capsule chamber. The capsule and/or capsule chamber may be configured such that the capsule makes repetitive right angle impacts with one or more capsule chamber walls. Right angle impacts of the capsule with the device walls can maximize impaction force and improve dispersion of the drug from the capsule. An optimized inhaler design having a capsule motion in a plane perpendicular to airflow direction is developed in the study of Behara et al. (2013a) and termed $CC_1$-3D.

Figures 4A, 4B, 4C:
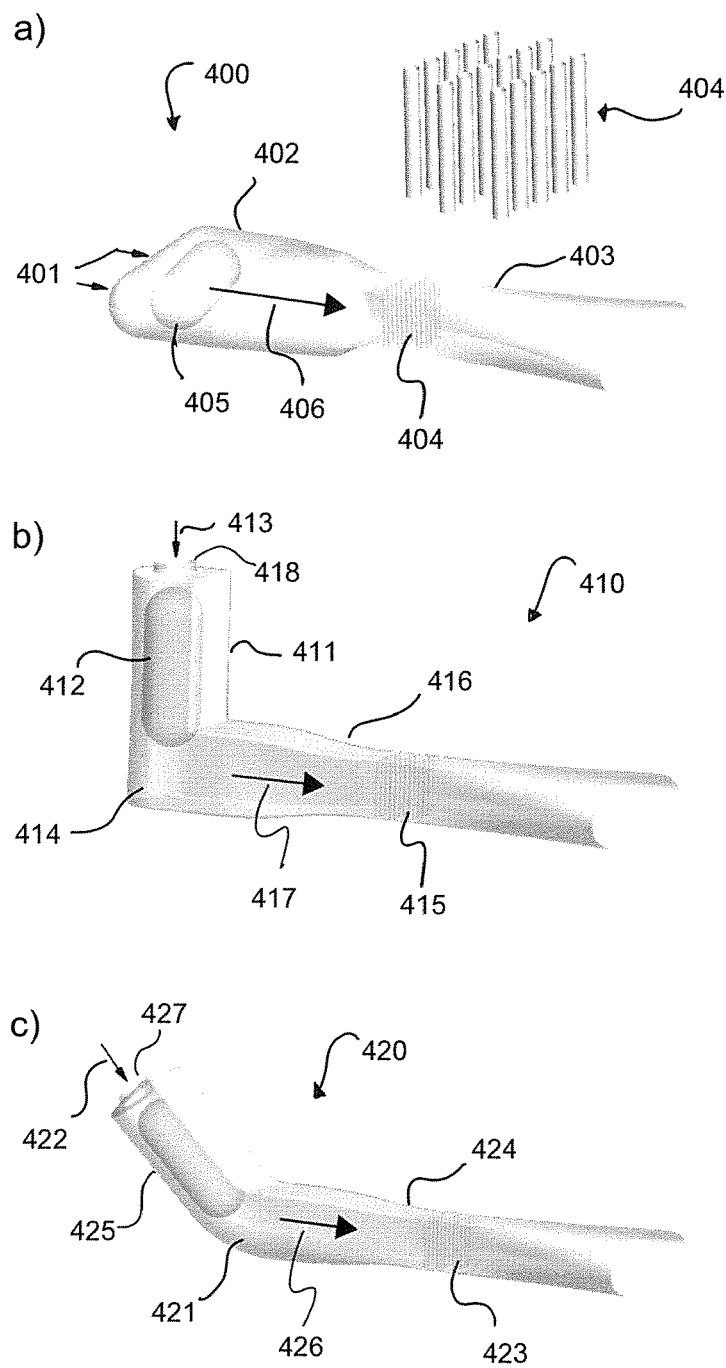
FIGS. 4a-4c. Dry powder inhalers (DPI) considered consisting of different capsule chambers (CC) coupled with the 3D rod array flow passage: (a) $CC_1$-3D with two air inlets and the capsule oriented perpendicular to the inlet airflow; (b) $CC_L$-3D with the capsule oriented parallel to the inlet airflow and a 90° angle between the CC and flow passage; and (c) $CC_A$-3D with a 45° angle between the CC and flow passage.

Various shapes or arrangements of the spaces which define or affect the flow path through a DPI device will occur to one of ordinary skill in the art in the practice of the invention. For example, FIGS. 4a-4c illustrate possible configurations which may be used. FIG. 4a shows a schematic for a DPI device 400 in which there is a generally linear arrangement of air inlets 401, capsule chamber 402, and flow passage 403 comprising a 3D rod array 404. Furthermore the capsule chamber 402 is configured to hold the capsule 405 perpendicular with the flow direction 406.

FIG. 4b shows a schematic for a DPI device 410 in which there is an L-shaped capsule chamber 411 which is configured to hold a capsule 412 parallel with the flow direction 413. In the embodiment shown, an L-shaped capsule chamber 411 holds the capsule 412 parallel with the inlet flow direction 413, has a semi-circular cross-section with one flat side, and routes the flow through a 90° bend 414. By routing the flow through the 90° bend prior to it passing through a 3D rod array 415 in a flow passage 416, the nondimensional specific dissipation (NDSD) defined by Longest et al. (2013) may be increased, which may increase deaggregation and decrease the MMAD. The parallel flow passage (that is to say, the passage configured to orient the capsule parallel with the direction of air flow 413) together with the shape of the capsule chamber 411 increase emitted dose compared with the $CC_1$-3D design, which is demonstrated in the study of Behara et al. (2013b).

An embodiment of a DPI device may comprise one or more air inlets, a capsule chamber associated with at least one of the one or more air inlets for receiving a capsule containing a dry powder; and an aerosol delivery port configured for the egress of air which has passed through the capsule chamber. The capsule chamber may be configured to orient a primary capsule axis of a capsule perpendicular to a primary direction of air flow in the capsule chamber and allow for vibratory motion of the capsule.

In an alternative embodiment, the capsule chamber may be configured to orient a primary capsule axis parallel to a primary direction of air flow in the capsule chamber. As shown in FIGS. 4b and 4c, a longitudinal axis of the capsule chamber 411 or 425 may be configured at an inclined angle to a downstream flow path 417 or 426, respectively, between said capsule chamber and said aerosol delivery port. In some embodiments a capsule chamber may be configured to angle flow direction by any amount from 0° to 90°. FIG. 4c shows a schematic of a DPI device 420 with an angle 421 after inlet flow direction 422 of approximately 45°. A 3D rod array 423 may be positioned in a flow passage 424 preferably after the bend 421.

A variety of air sources which may be used in the practice of the invention will occur to those skilled in the art. For instance, in respect to FIGS. 4a-4c, air inlets 401, 418, and 427 may simply deliver air from the user's inspiratory effort during inhalation. Alternatively, one or more air inlets may comprise or be associated with an external airflow source (see FIG. 3), such as a ventilation bag, a syringe, or a compressed air source.

Generally, an aerosol delivery port is an outlet from which air with entrained dry powder particles may be delivered by a drug delivery system or device to a user. In particular, delivery may be carried out using a mouthpiece that is inserted directly into the mouth, by using a mask that fits over the nose and mouth, intranasally, e.g. using tubes that direct the flow into the nasal passage, or even using longer tubes that deliver the flow into the throat or directly into the lungs.

Figures 5A, 5B:
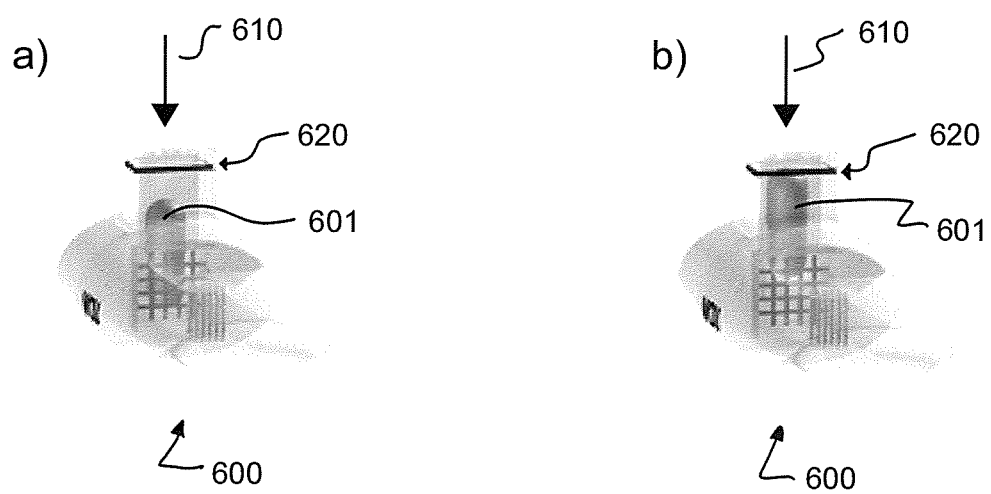
FIGS. 5a and 5b. The $CC_2$-3D inhaler with the capsule in the (a) loaded (no flow), and (b) in-use (45 LPM) position. An optimum flow rate of 45 LPM is required to elevate a capsule containing 2 mg of powder above the red line marked in the capsule viewing window FIG. 6. Non-dimensional specific dissipation (NDSD) vs. $FPF_{1\ \mu m}$ for eight inhalers considered at different inhalation flow rates (45-70 LPM) using a proprietary spray dried powder formulation. The high degree of correlation indicates that NDSD is largely responsible for the breakup of aerosol agglomerates and the formation of particles with submicrometer sizes. Maximum NDSD and $FPF_{1\ \mu m}$ occurred for the 3D array design disclosed in this invention.

Now in reference to FIGS. 5a-5b, in another embodiment, the invention provides visual feedback for determination of correct inhalation flow rate. The feedback may be provided by the capsule chamber of a DPI device 600, preferably an L-shaped capsule chamber that may increase emitted dose, increase dispersion (decrease MMAD), and provide visual feedback in view of the patient or health care professional with correct inhalation flow rate. In FIGS. 5a-5b there is shown an L-shaped capsule chamber that holds the capsule 601 parallel with an inlet flow direction 610, has a semi-circular cross-section with one flat side, and routes the flow through a 90° bend. DPI performance is known to be influenced by the rate of inhalation through the device. Therefore, it is important for the patient to receive easy to understand feedback on the use of a correct flow rate. A capsule chamber which is preferably an L-shaped capsule chamber positions the capsule within view of the patient during usage. The capsule chamber may be configured such that higher flow rates cause the capsule to rise in the capsule chamber, which has a capsule-retaining portion which is longer than the capsule. When sufficient flow is generated for effective deaggregation, the capsule rises to a certain marked level 620 or other indicia in view of the patient. Generally the visual feedback is associated with the position of the capsule or a part of the capsule (e.g. the end of the capsule) within the capsule chamber. In this manner, the patient can be shown that a correct inhalation flow rate was employed and that a more accurate or correct dosage was received. In the practice of the invention sufficient flow rate may vary depending on variables such as patient age and type of powder being inhaled. The relative sizes and shapes of the capsule chamber and/or a capsule for loading into the capsule chamber may be selected according to a target flow rate. The configuration would be generally such that when the target flow rate is present, the end of the capsule aligns with the marked level.

In short, in some embodiments of a DPI device there may be included one or more air inlets, a chamber associated with at least one of the air inlets and which is configured to receive a capsule containing a dry powder, an aerosol delivery port configured for the egress of air which has passed through the chamber, and an indicator associated with the chamber for indicating a position of the capsule within the chamber. The air inlets, chamber, and aerosol delivery port are configured such that the position of the capsule within the chamber is a function of inhalation flow rate. The indicator is preferably a viewing window in a wall of the capsule chamber for viewing a position of the capsule within the chamber while using the inhaler. The viewing window is preferably arranged or positioned in view of a user during inhalation. There is generally indicia associated with the indicator for indicating simply and clearly when a proper flow rate is occurring.

In yet another embodiment, the invention includes a coating or coatings of a capsule (or drug containing unit), capsule chamber, and/or inhaler with low surface energy compounds to improve emitted dose. Adhesive forces between the aerosol particles and surfaces are known to reduce device emptying and decrease powder dispersion. Contact forces between the capsule and inhaler may reduce vibrational frequency and emitted dose. In the practice of the invention low surface energy materials may be used to coat inhaler device components for increased emitted dose and increased powder dispersion (decreased MMAD) of an aerosol. The coating may be on the inside of a capsule containing the powder (or a blister or powder containment unit), outside of the capsule, and/or walls of the inhaler. Interior coating of the capsule can reduce adhesion and capsule retention of the drug powder thereby increasing emitted dose. Exterior capsule coating and coating of the capsule chamber can reduce powder attachment and surface forces during capsule vibration and capsule-to-wall impactions. High capsule vibration frequency is generally important for effective deaggregation of the aerosol. Alternatively, the capsule and/or capsule chamber can be constructed from low surface energy materials. Coatings structures that contain drug powder on external surfaces, such as balls, rods, or capsules, with low surface energy materials to improve emitted dose is also disclosed.

Low surface energy can refer to materials that have a high contact angle with water droplets. Current plastics for inhaler construction include polyamide, polypropylene, and polyethylene, which have water contact angles up to approximately 100 degrees (Zisman 1964). Current capsule materials (gelatin and HPMC) have contact angles lower than these values. Low surface energy coatings and materials for improved device emission can be classified as having a water contact angle ≥105 degrees. For example, PTFE has a reported water contact angle of 110 degrees (Zisman 1964). Superhydrophobic surfaces are defined as having a water contact angle of 150 degrees. Coating with superhydrophobic materials to improve emitted dose is also disclosed. The study of Behara et al. (2013a) demonstrates improving emitted dose and reducing MMAD with low surface energy coatings. The effects of coating is demonstrated for submicrometer and micrometer sized primary particles.

Submicrometer combination particle DPI formulations are provided that include/incorporate one or more drugs/medicaments, one or more hygroscopic excipients, one or more dispersion agents, and one or more surface active agents into a combination particle. Generally, the ratio of each component can be optimized to ensure maximize drug load and optimal dispersibility. In some embodiments the DPI formulations are for EEG applications, in which case the ratio of each component of the formulations is preferably optimized for the desired hygroscopic growth for the EEG application.

Medicaments—such as drugs, therapeutic agents, and active agents—that may be formulated with a hygroscopic excipient as described herein or delivered as described herein include but are not limited to various agents, drugs, compounds, and compositions of matter or mixtures thereof that provide some beneficial pharmacologic effect. Drugs or agents which may be used include agents for the treatment of asthma and other respiratory disorders, anesthesia agents, nucleic acid molecules, anti-pain agents, anti-inflammation agents, anti-depressants and other mood altering drugs, anti-viral agents, anti-bacterial agents, anti-fungal agents, anti-cancer agents, hormones, benzodiazepines and calcitonin. The particles of the invention broadly encompass substances including "small molecule" drugs, vaccines, vitamins, nutrients, aroma-therapy substances, and other-beneficial agents. As used herein, the terms further include any physiologically or pharmacologically active substance that produces a localized or systemic effect in a patient, i.e. the agent may be active in the lung, or may be delivered to the lung as a gateway to systemic activity.

In some embodiments, the site of action of the substance that is delivered may be the lung itself. Examples of such agents include but are not limited to agents for anesthesia; treatments for asthma or other lung conditions; anti-viral, anti-bacterial or anti-fungal agents; anti-cancer agents; α-1 antitrypsin and other antiproteases (for congenital deficiencies), rhDNAse (for cystic fibrosis), and cyclosporine (for lung transplantation), vaccines, proteins and peptides, etc. Other examples include bronchodilators including albuterol, terbutaline, isoprenaline and levalbuterol, and racemic epinephrine and salts thereof; anti-cholinergics including atropine, ipratropium bromide, tiatropium and salts thereof; expectorants including dornase alpha (pulmozyme) (used in the management of cystic fibrosis; corticosteroids such as budesonide, triamcinolone, fluticasone; prophylactic anti-asthmatics such as sodium cromoglycate and nedocromil sodium; anti-infectives such as the antibiotic gentamicin and the anti-protozoan pentamidine (used in the treatment of *Pneumocystis carinii* pneumonia), and the antiviral agent ribavirin, used to treat respiratory syncytial virus e.g. in young children and infants.

However, this need not be the case. Some agents delivered via the deep lung into systemic circulation will be distributed systemically via the circulatory system. Examples of such agents include but are not limited to, for example, calcitonin (for osteoporosis), human growth hormone (HGH, for pediatric growth deficiency), various hormones such as parathyroid hormone (PTH, for hyperparathyroidism), insulin and other protein or peptide agents, nucleic acid molecules, and anti-pain or anti-inflammation agents. Such agents may require chronic administration.

In another example, it may be desirable to target areas for the lungs to delivery of therapeutic agents. In this example, anti-infective agents may be required to treat localized lung infections within the airways. Targeting to specific regions within the lung and delivering drug aerosols with high deposition efficiencies may be possible with this invention. Once a target region has been identified (through clinical examination), an aerosol would be produced that would have a final particle size suitable for deposition in that region. In this example, an initially nano-sized aerosol would be formulated with appropriate hygroscopic excipients and inhaled. By controlling the amount of hygroscopic excipients present in the aerosol formulation, it is possible to control the final particle size of the aerosol and therefore ultimately its site of deposition within the lung.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfioxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracycline, including tetracyclin, oxytetracyclin, rolitetracyclin, minocyclin, doxycycline, tigecycline and aminocycline; glycopeptides, including vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofluvin, tonoftal, naftifin, terbinafin, amorolfin, ciclopiroxolamin, echinocandins, such as micafungin, caspofungin, anidulafungin; nitrofurans, including nitrofurantoin and nitrofuranzone; -polyenes, including amphotericin B, natamycin, nystatin, flucocytosine; other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine; antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, alphahederin, bisabolol, lycopodin, vitapherole; wound healing compounds including dexpantenol, allantoin, vitamins, hyaluronic acid, alpha-antitrypsin, anorganic and organic zinc salts/compounds, interferones (alpha, beta, gamma), tumor necrosis factors, cytokines, interleukins.

In a similar way to that described for targeting antibiotics, it may also be desirable to target anti-cancer compounds or chemotherapy agents to tumors within the lungs. It is envisaged that by formulating the agent with an appropriate hygroscopic growth excipient, it will be possible to target regions of the lung where it has been identified that the tumor is growing. Examples of suitable compounds are immunmodulators including methotrexat, azathioprine, cyclosporine, tacrolimus, sirolimus, rapamycin, mofetil, cytotatics and metastasis inhibitors, alkylants, such as nimustine, melphanlane, carmustine, lomustine, cyclophosphosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinum, cis-platinum and metallocene compounds such as titanocendichloride; amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab may be added.

Additional active agents may be selected from, for example, hypnotics and sedatives, tranquilizers, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents (particularly those that target lung cancer), antithrombotic agents, antihypertensives, cardiovascular drugs, antiarrhythmics, antioxicants, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically. The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of other active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hoiinone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, and 13-cis retinoic acid, and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated fauns, and biologically active fragments and analogs thereof. Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense and inhibitory RNA. Further, an active agent may comprise live attenuated or killed viruses suitable for use as vaccines. Other useful drugs include those listed within the Physician's Desk Reference (most recent edition).

An active agent for delivery or formulation as described herein may be an inorganic or an organic compound, including, without limitation, drugs which act on: the lung, the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Frequently, the active agent acts in or on the lung.

The amount of active agent in the pharmaceutical dry powder formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of hygroscopic excipient contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

Hygroscopic excipients which may be used in the practice of the invention include mannitol, sodium chloride, sodium citrate, citric acid, potassium chloride, zinc chloride, calcium chloride, magnesium chloride, potassium carbonate, potassium phosphate, carnallite, ferric ammonium citrate, magnesium sulfate, sodium sulfite, calcium oxide, ammonium sulfate; sugars such as sorbital, mannitol, glucose, maltose, galactose, fructose, sucrose; glycols such as polyethylene glycols (varying molecular weights), propylene glycol, glycerol; organic acids such as citric acid, sulfuric acid, malonic acid, adipic acid; lactams such as 2-pyrrolidone, polyvinylpolyprrolidone (PVP); and other substances including potassium hydroxide, sodium hydroxide, gelatin, hydroxypropyl methylcellulose, pullalan, starch, polyvinyl alcohol, and sodium cromoglycate.

Dispersion agents which may be used in the practice of the invention include L-leucine, D-leucine, isoleucine, lysine, valine, methionine, cysteine, phenylalanine and magnesium sterate. Surface active agents which may be used in the practice of the invention include poloxamer 188, polysorbates (Tween™), sodium dodecyl sulfate, polyethoxylated alcohols, polyoxyethylene sorbitan, polyoxyl 10 lauryl ether, Brij 721™, nonylphenol ethoxylate, and lecithin. An exemplary formulation comprises albuterol sulfate, mannitol, L-leucine, and poloxamer 188, preferably in a ratio of 30:48:20:2 for the four respective components of the submicrometer combination particle DPI formulations. In the Examples below this is identified as formulation R06.

The Examples below show these formulations forming aerosols with high FPF and MMAD near 1 μm. Individuals of ordinary skill in the art and therefore familiar with DPI performance will recognize that these formulations result in performance that is significantly better than any existing DPI in terms of high FPFs and very small MMADs with similar or improved device emptying. Quantitative results are provided for novel formulations which have been employed in commercially available DPIs, in commercial DPIs with the addition of our 3D rod array, or in combination with our novel DPIs, termed capsule chamber and 3D rod array (CC-3D) including a capsule chamber for perpendicular capsule alignment ($CC_1$-3D), parallel alignment with viewing window using an L-shaped capsule chamber ($CC_L$-3D), and parallel alignment with viewing window using an angled capsule chamber ($CC_A$-3D). It should also be recognized that although model/exemplary drugs and model/exemplary excipients are shown, further drug:excipient submicrometer combination particles could be produced by those skilled in the art in the practice of the invention. In addition, while spray drying is generally used as the particle production technique for the formulations, those skilled in the art will recognize that a number of other particle production techniques could similarly be utilized to generate these submicrometer combination particle formulations for inhalation. Examples are also included which demonstrate the superior performance of the CC-3D inhalers with conventional commercial powder formulations.

The subjects which are the end-users of the methods and devices of the invention are generally mammals, and are usually humans, although this need not always be the case. Veterinary applications of this technology are also contemplated.

EXAMPLES

Example 1

Improvement of Existing Device with a 3-D Array of Rods

Table 1 shows the aerosolization characteristics of a proprietary spray dried submicrometer powder drug formulation in both active and passive DPIs (Son et al., 2012). The aerosolization characterization results indicated the relative efficiency of the DPIs to disperse the formulation to primary drug particles for inhalation. State-of-the-art active DPIs are considered first and produced very low $FPF_{1\ \mu m}$ (less than 10%) for this submicrometer formulation. State-of-the art passive DPIs improved dispersion using the Aerolizer and HandiHaler producing $FPF_{1\ \mu m}$ of the emitted dose (ED) of 28.3 and 19.5%, respectively. In the final row of the table, the flow passage of the HandiHaler device (FIG. 1a) was replaced with a flow passage containing a 3D rod array of rods (FIG. 1e) as disclosed in this invention. The HandiHaler with the modified 3D array results in a 2× increase in $FPF_{1\ \mu m}$ and a significant reduction in drug MMAD (Table 1) without a significant change in emitted dose (ED) for this submicrometer formulation. Both the HandiHaler and HandiHaler with 3D array were operated at 45 LPM, which is typical for patient usage.

TABLE 1

Effect of DPI on the proprietary spray dried combination formulation drug aerosolization characteristics (values are means +/− SD, n = 3) (Son et al., 2012; Son et al., 2013b)

| Device | ED (%) | $FPF_{5\ \mu m/ED}$ (%) | $FPF_{1\ \mu m/ED}$ (%) | MMAD (μm) | MMD (μm) |
|---|---|---|---|---|---|
| Active DPIs | | | | | |
| Spiros | 73.4 (4.1) | 80.2 (3.1) | 6.8 (0.6) | 2.55 (0.06) | 2.21 |
| Exubera | 62.8 (3.1) | 96.3 (0.7) | 9.6 (0.5) | 1.95 (0.04) | 1.69 |
| Passive DPIs | | | | | |
| Aerolizer | 81.4 (2.0) | 95.3 (1.1) | 28.3 (3.1) | 1.40 (0.05) | 1.22 |
| HandiHaler | 78.2 (2.7) | 87.6 (3.6) | 19.5 (3.1) | 1.60 (0.09) | 1.39 |
| HandiHaler with 3D rod array (present invention) | 74.2 (1.4) | 97.3 (0.3) | 38.8 (6.3) | 1.13 (0.05) | 0.98 |

Example 2

Correlation of FPF with Turbulence (Longest et al., 2013)

It is known that turbulence in the inhaler increases the deaggregation of particles in some cases (Voss and Finlay 2002). However, previous correlations between FPF and turbulence level have been weak. A new parameter is proposed for the design of DPIs to quantify the form of turbulence most responsible for aerosol breakup in the inhaler. The 3D rod array inhaler will be shown to optimize this form of turbulence.

In turbulence, the specific dissipation rate is typically defined as (Wilcox 1998)

$$\omega = \frac{k^{1/2}}{C_\mu^{1/4} \ell} \quad (1)$$

where k is the turbulent kinetic energy [m²/s²], $C_\mu$ is a constant equal to 0.09, and l is the characteristic eddy length scale [m]. The ω parameter captures both kinetic energy available for breakup along with eddy length scale, with smaller eddies being more effective at breaking up small aggregates and increasing FPF. For an inhaler geometry, the volume-averaged specific dissipation is calculated as $$\bar{\omega} = \frac{1}{V} \int_V \omega_{CV} \, dV \quad [1/s] \quad (2)$$

where V is the volume of the flow passage available for breakup and $\omega_{CV}$ is the local ω value in individual voxels, or control volumes (CVs), composing the geometry. It is also found that exposure time $\bar{\omega}$ also increases the amount of agglomerate breakup, and is calculated as $$t_{exposure} = \frac{V}{Q} \quad [s] \quad (3)$$

where Q is flow rate through the flow passage and V is an approximate passage volume. The non-dimensional specific dissipation is then developed as $$NDSD = \bar{\omega} t_{exposure} \quad (4)$$

This parameter captures both the strength of the turbulence most responsible for aerosol breakup ($\bar{\omega}$) as well as the exposure time to $\bar{\omega}$.

Eight different flow pathways with different turbulent dispersion mechanisms were constructed and attached to the HandiHaler capsule dispersion chamber. Flow rates considered ranged from 45-75 LPM. Mechanisms of increasing turbulence in the flow passage included a constriction tube, impaction surface, 2D mesh, jets, and a 3D rod array (FIGS. 1a-1e, respectively).

Figure 6:
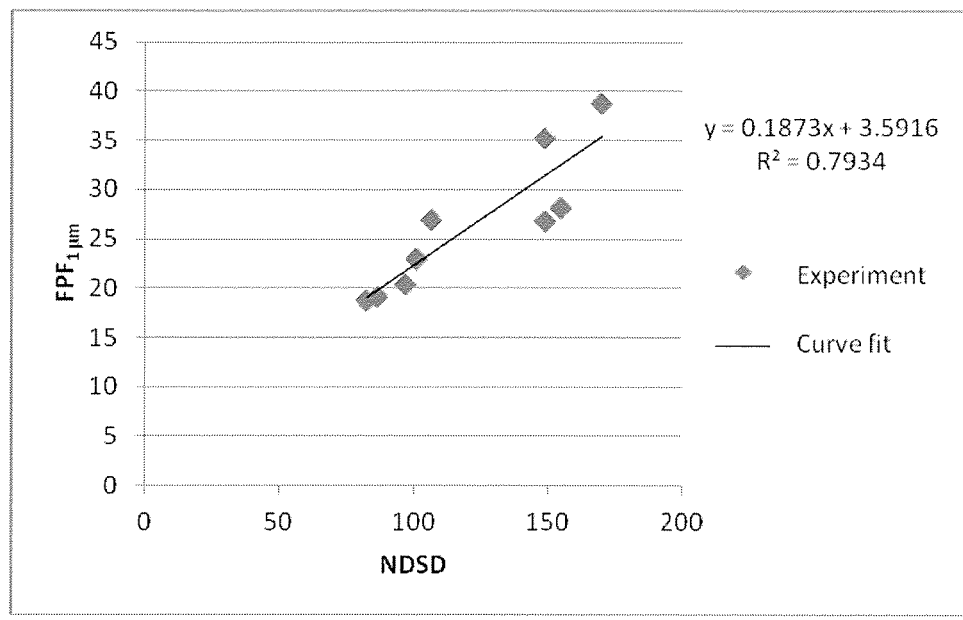

In vitro experiments were conducted using a proprietary spray dried submicrometer drug powder formulation to quantify $FPF_{1\ \mu m}$. CFD simulations were conducted on each inhaler to predict NDSD under flow conditions identical to the experiments. A high degree of correlation was found between the NDSD and $FPF_{1\ \mu m}$ (FIG. 6), as indicated by a correlation coefficient of $R^2=0.79$. For the systems considered, the 3D array flow passage had the highest $FPF_{1\ \mu m}$, $FPF_{5\ \mu m}$, and NDSD (Longest et al., 2013) for the drug aerosol. The 3D array, disclosed in this invention, was also the only system that generated a high fine particle fraction aerosol.

Example 3

Inhaler Performance at a Constant Flow Rate

One method to compare inhaler performance on a consistent basis is to consider all devices of interest at the same flow rate. The existing flow passage of the HandiHaler (small diameter or constricted tube) was considered along with turbulence inducing flow passages containing an impaction surface (FIG. 1b), 2D mesh (FIG. 1c), jets (FIG. 1d), and 3D array of rods (FIG. 1e). All systems were operated at 45 LPM to aerosolize a proprietary spray dried submicrometer drug powder formulation. In vitro experiments of exiting drug aerosol size were conducted based on impactor testing and drug quantification using high performance liquid chromatography (HPLC). In vitro results along with CFD predictions of NDSD are reported in Table 2. Based on these results at a constant flow rate, the 3D rod array maximizes $FPF_1$ and $FPF_{5\ \mu m}$ for the drug aerosol. The 3D rod array was also the only inhaler to generate a submicrometer aerosol based on geometric mean particle diameter (mass median diameter: MMD<1 μm). Submicrometer conditions required that NDSD be greater than approximately 150. It is not obvious that a 3D array will significantly increase NDSD and provide better aerosol dispersion than other devices, including a 2D mesh, evaluated at the same flow rate.

TABLE 2

Aerosol characteristics of a proprietary spray dried drug powder formulation aerosolized with different flow passages (FIGS. 1a-e) attached to the HandiHaler capsule chamber and tested at a flow rate of 45 LPM. Standard deviation values are provided in parentheses.

| Device | Device Retention (%) | FPF$_{5\ \mu m/ED}$ (%) | FPF$_{1\ \mu m/ED}$ (%) | MMAD ($\mu$m) | MMD ($\mu$m) | NDSD |
|---|---|---|---|---|---|---|
| Constriction tube | 21.8 (1.7) | 89.5 (3.2) | 18.8 (0.5) | 1.55 (0.02) | 1.35 | 82.6 |
| Impaction surface | 20.1 (2.0) | 95.8 (0.5) | 26.8 (3.8) | 1.39 (0.10) | 1.21 | 148.4 |
| 2D mesh | 26.0 (3.4) | 94.5 (2.6) | 19.2 (4.7) | 1.56 (0.08) | 1.36 | 86.5 |
| Inward facing jets (45 LPM over capsule) | 19.3 (1.8) | 95.9 (0.7) | 26.9 (6.0) | 1.46 (0.16) | 1.27 | 110.8 |
| 3D array of 0.5 mm rods (present invention) | 25.8 (1.4) | 97.3 (0.3) | 38.8 (6.3) | 1.13 (0.05) | 0.98 | 169.7 |

Example 4

Inhaler Performance at a Constant Pressure in the Flow Passage

A second method to consistently compare inhaler performance is to consider the devices at a constant pressure drop. As with the previous study, flow passages were connected to the HandiHaler capsule chamber to increase turbulence and included the inward jet model, 2D mesh, and 3D array. Flow rates were adjusted to achieve a pressure drop of 2 kPa over the flow passages, illustrated in FIGS. 1a-1e, with values reported in Table 3. The total device pressure drop was around 4 kPa. The formulation tested was a proprietary spray dried submicrometer drug powder formulation. In vitro experiments of exiting drug aerosol size were conducted based on impactor testing and drug quantification using high performance liquid chromatography (HPLC). In vitro results along with CFD predictions of NDSD are reported in Table 3. At a constant pressure drop of 2 kPa in the flow passage, performance of the 3D array is again superior to the other designs in terms of increasing drug aerosol FPF and reducing MMAD. It is not obvious that a 3D rod array will significantly increase NDSD and provide better aerosol dispersion than other devices, including a 2D mesh, evaluated at the same pressure drop. Again, an NDSD value>150 was required to produce the best high fine particle aerosol observed.

TABLE 3

Aerosol characteristics for different flow passages (see FIGS. 1a-1e) attached to the HandiHaler capsule chamber evaluated at a pressure drop of 4 kPa over the flow passage. Standard deviation values are provided in parentheses.

| Device | Flow rate (LPM) | Device Retention (%) | FPF$_{5\ \mu m/ED}$ (%) | FPF$_{1\ \mu m/ED}$ (%) | MMAD ($\mu$m) | MMD ($\mu$m) | NDSD |
|---|---|---|---|---|---|---|---|
| 2D mesh | 53 | 18.8 (0.9) | 97.2 (0.9) | 24.1 (3.2) | 1.43 (0.04) | 1.24 | 79.3 |
| Inward facing jets | 75 (total) 45 (over capsule) | 19.3 (1.8) | 95.9 (0.7) | 26.9 (6.0) | 1.46 (0.16) | 1.27 | 110.8 |
| 3D array of 0.5 mm rods$^a$ (present invention) | 45 | 25.8 (1.4) | 97.3 (0.3) | 38.8 (6.3) | 1.13 (0.05) | 0.98 | 169.7 |

$^a$Values evaluated at 1.9 kPa and were unchanged through 3.1 kPa

Example 5

Effect of Inhaler Piercing vs. Pre-Piercing Capsules

In this example, the HandiHaler device was again considered. Capsules pierced with the HandiHaler mechanism vs. pre-pierced capsules were considered. Pre-piercing allows for the use of a smaller needle and better placement of the holes. The formulation tested was a proprietary spray dried submicrometer drug powder formulation. In vitro experiments of exiting drug aerosol size were conducted based on impactor testing and drug quantification using high performance liquid chromatography (HPLC). Table 4 indicates significant improvement in the drug aerosol FPF for the per-pierced capsules.

TABLE 4

Capsules pierced with the Handihaler vs. pre-pierced capsules used in the Handihaler device operated at 45 LPM. Standard deviation values are provided in parentheses.

| Device | ED (%) | FPF$_{5\ \mu m/ED}$ (%) | FPF$_{1\ \mu m/ED}$ (%) | MMAD ($\mu$m) | MMD ($\mu$m) |
|---|---|---|---|---|---|
| Handihaler pierced | 78.2 (3.6) | 87.6 (3.6) | 19.5 (3.1) | 1.6 (0.1) | 1.39 |
| Pre-pierced (present invention) | 78.9 (3.1) | 94.6 (1.1) | 24.5 (0.5) | 1.5 (0.0) | 1.30 |

Example 6

Performance of the CC$_1$-3D Inhaler

A device that includes the three DPI innovations of a 3D array, pre-pierced capsules, and capsule motion perpendicular to flow (capsule chamber 1; CC$_1$) was designed and prototyped (FIG. 3). Capsule piercing consisted of two holes approximately 1 cm from the center. Performance of the inhaler was assessed in terms of drug aerosol size from impactor testing using HPLC and a proprietary spray dried submicrometer drug powder formulation. Table 5 compares the device performance with current active and passive DPIs using the same powder formulation. Clearly, the novel components of the CC$_1$-3D create a new device that can produce a highly disperse aerosol. Performance of the CC$_1$-

3D was measurably better than all commercial active and passive devices considered except for the Aerolizer. Performance of the $CC_1$-3D device was similar to the Aerolizer, but at a much lower flow rate. Lower flow rates are often advantageous for DPI delivery to patients with unhealthy lungs, children, and to improve lung deposition. Therefore, the lower flow rate of the $CC_1$-3D combined with similar drug aerosol FPFs and MMD compared with the Aerolizer indicate improved performance of the $CC_1$-3D design.

It is not obvious that the new device consisting of a 3D array and a new form of capsule motion can improve inhaler performance in terms of increasing drug aerosol FPF and decreasing MMAD compared with current active (complex) and passive state-of-the-art devices.

TABLE 5

Comparison of active and passive current state-of-the-art DPIs with the $CC_1$-3D. Data on all devices except for the $CC_1$-3D is from Son et al. (2012).

| Device | Flow rate (L/min) | $FPF_{5\ \mu m/ED}$ (%) | $FPF_{1\ \mu m/ED}$ (%) | MMAD (μm) | MMD (μm) |
|---|---|---|---|---|---|
| Active DPIs | | | | | |
| Spiros | 30 | 80.2 (3.1) | 6.8 (0.6) | 2.55 (0.06) | 2.21 |
| Exubera | 30 | 96.3 (0.7) | 9.6 (0.5) | 1.95 (0.04) | 1.69 |
| Passive DPIs | | | | | |
| Aerolizer | 80 | 95.3 (1.1) | 28.3 (3.1) | 1.40 (0.05) | 1.22 |
| HandiHaler | 45 | 87.6 (3.6) | 19.5 (3.1) | 1.60 (0.09) | 1.39 |
| $CC_1$-3D (present invention) | 50 | 95.5 | 28.7 | 1.34 | 1.16 |

Example 7

Effects of Materials: 3D Rod Array and PTFE Coating

In order to improve powder deaggregation, the resin 3D rod array in the flow passage of the $CC_1$-3D inhaler was replaced by a metal (stainless steel) 3D rod array to form the $CC_1$-3Dm inhaler. Both the $CC_1$-3D and $CC_1$-3Dm inhalers were tested for aerosolization performance with a new batch of the proprietary spray dried submicrometer drug powder formulation (EEG formulation batch 2), and results are presented in Table 6. In a separate device, the capsule and internal flow passages of the $CC_1$-3Dm inhaler were also coated with PTFE and tested. Coated surfaces included both the inside and outside of the capsule, the capsule chamber, and flow passage containing the 3D rod array. The powder formulation was previously optimized by Son et al. (2013a) and consisted of albuterol sulfate, mannitol, L-leucine, and poloxamer 188 in a mass ratio of 30:48:20:2 formed through a spray drying process. Capsules were loaded with 2 mg of powder and pierced with a 0.5 mm needle, placed in the inhalers, and actuated at a flow rate of 50 LPM. Dose remaining in the inhaler components, capsule, and emitted dose were determined with a validated HPLC method. The aerosol was characterized using cascade impaction with a Next Generation Impactor and masses of drug on each stage were quantified using HPLC.

Small differences in the performance of $CC_1$-3D with the resin array are observed between the result presented in Tables 5 and 6. These differences are due to batch to batch variability in the spray dried powder. Despite using the same operating conditions with the spray dryer, it is well known that there may be differences in spray droplet size distribution and thus the final product particle size distribution.

Replacing the resin array ($CC_1$-3D) with the metal array ($CC_1$-3Dm) did not alter the resistance of the mouthpiece. In comparing $CC_1$-3D resin and metal arrays (Table 6) at a 4 kPa pressure drop (50 LPM), the $CC_1$-3Dm design demonstrated significantly lower flow passage retention (p<0.001), smaller MMAD (p=0.003) and higher $FPF_{<1\ \mu m/ED}$ (p=0.003) compared to the resin rod array version. The improved performance of the metal array design was likely due to either increased particle rebound from the metal vs. resin surfaces or improved structural integrity of the array with metal construction. Based on the successful use of metal rods in the 3D array, this design is used in the remaining case studies reported for this invention, and is referred to simply as the $CC_1$-3D inhaler.

Considering low surface energy coating, it was found that the PTFE coating produced significantly lower capsule and $CC_1$ drug retention (p<0.001) (Table 6). This increased the emitted dose of the $CC_1$-3Dm with PTFE to 81.4±2.2 compared to 64.7±1.5% without coating (p<0.001). As a result, the final optimized device was determined to be the $CC_1$-3Dm design with PTFE coating, which produced $FPF_{1\ \mu m/ED}$ and $FPF_{5\ \mu m/ED}$ of 92.7% and 36.8%, an emitted dose of greater than 80% and a final MMAD of 1.3 μm.

TABLE 6

Aerosolization performance and drug deposition (n = 3; Mean ± standard deviation) of $CC_1$ with resin and metal 3D rod arrays and with a low surface energy coating of the capsule and inhaler at a flow rate of 50 LPM.

| Description | $CC_1$-3D plastic | $CC_1$-3D metal | $CC_1$-3Dm PTFE coating |
|---|---|---|---|
| Capsule retention (%) | 14.1 ± 1.3 | 16.2 ± 0.7 | 7.3 ± 1.0 |
| Flow passage retention (%) | 13.2 ± 0.4 | 10.2 ± 0.4 | 9.1 ± 1.4 |
| CC retention (%) | 8.8 ± 1.4 | 8.8 ± 1.0 | 2.2 ± 0.6 |
| Emitted (%) | 63.8 ± 1.9 | 64.7 ± 0.5 | 81.4 ± 2.2 |
| $FPF_{5\ \mu m/ED}$ (%) | 93.9 ± 0.4 | 94.5 ± 0.8 | 92.7 ± 1.2 |
| $FPF_{1\ \mu m/ED}$ (%) | 32.2 ± 1.0 | 37.3 ± 1.0 | 36.8 ± 0.8 |
| MMAD (μm) | 1.44 ± 0.03 | 1.30 ± 0.02 | 1.30 ± 0.01 |

Example 8

Effects of Perpendicular Capsule Orientation ($CC_1$-3D) Vs. an L-Shaped Capsule Chamber ($CC_L$-3D)

The objective of this study was to compare performance of the optimized inhaler that orients the capsule primary axis perpendicular to airflow ($CC_1$-3D) with two versions of a new high efficiency DPI containing an L-shaped capsule chamber. This new design is intended to maximize emitted dose and increase turbulence in the 3D rod array to further improve deaggregation. Comparisons of the three devices are initially performed using computational fluid dynamics (CFD) simulations and the previously developed NDSD parameter that correlated with deaggregation of carrier-free formulations (Longest et al., 2013). CFD estimates of inhaler performance are then verified with in vitro experiments, and the quality of the drug aerosol from each inhaler is evaluated.

The three DPI designs considered in this study are illustrated in FIGS. 4a to 4c. Each DPI employs the 3D rod array and flow passage geometry. This flow passage design was shown to maximize the NDSD parameter, which was proven to quantitatively correlate with deaggregation for a carrier-free formulation across a series of eight inhalers evaluated at multiple flow rates (Example 2). The inhalers considered in this study differ based on the capsule chamber (CC) design. The first device was developed in Example 6 and 7, and orients the long axis of the capsule perpendicular to the incoming airflow (FIG. 4a). This DPI is referred to as $CC_1$-3D and includes metal rods in the 3D array, which were found to be more effective than plastic rods in Example 7. The new inhaler design employed in this example implements a capsule with the long axis aligned parallel with the incoming airflow. The capsule chamber is positioned at an angle to the downstream flow passage, and flow around this angle can accelerate the airstream entering the 3D array and increase the non-dimensional specific dissipation (NDSD), (Longest et al., 2013) thereby further improving aerosol deaggregation. This configuration has the added advantage of placing the capsule in view of the patient and raising the capsule when adequate flow is provided. The capsule chamber is semicircular, which is intended to increase instability in the flow stream around and capsule and enhance the strength of capsule-to-wall impactions. Two versions of the new inhaler are considered that implement either a 90° angle between the capsule chamber and flow passage, resulting in the L-shaped design ($CC_L$-3D; FIG. 4b) or an angled 45° design ($CC_A$-3D; FIG. 4c). In both $CC_L$-3D and $CC_A$-3D, a single air inlet is located above the capsule chamber with a diameter selected to produce a flow rate of 45-50 LPM at a pressure drop of 4 kPa. This resistance is equal to the $CC_1$-3D device with two air inlets, described in Example 6.

CFD simulations were performed to evaluate the NDSD parameter in each inhaler at a steady state flow rate of approximately 45 LPM. Simulations were conducted according to best practices as described in previous publications (Longest et al., 2013). In vitro experiments were conducted to evaluate the capsule and device retention, emitted dose, and aerosol characteristics based on the methods described in Example 7 using a proprietary spray dried submicrometer powder formulation.

CFD simulations of the NDSD parameter are displayed in FIGS. 5a-5c for the three inhalers considered. The maximum volume-averaged NDSD parameter occurs for the $CC_L$-3D design, arising from the acceleration of flow through the L-shaped capsule chamber. Table 7 reports performance of the three inhalers considered based on in vitro experiments conducted at 45-50 LPM. These experiments are based on the use of the same batch of powder. Considering emitted dose, the $CC_L$-3D inhaler had the highest value indicating that the $CC_L$ design provides effective motion of the capsule and aerosolization of the powder. The $CC_L$-3D design also provided the smallest MMAD, which is consistent with the NDSD predictions. In summary, the $CC_L$-3D design provided an MMAD ≤1.5 µm with a high submicrometer aerosol fraction ($FPF_{1\ \mu m/ED}$), an aerosol $FPF_{5\ \mu m/ED} \geq 90\%$, and emitted dose from the device ≥70%, which are consistent with high efficiency DPI performance.

Figure 7:
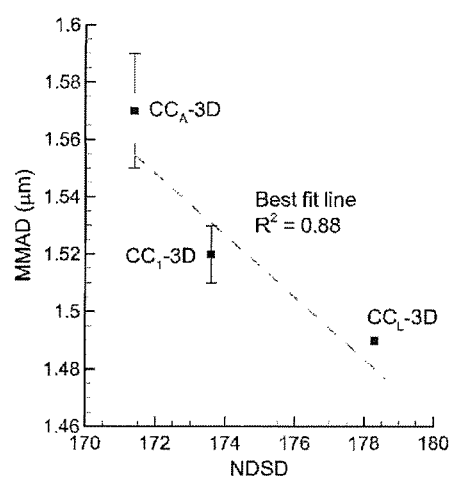
FIG. 7. Comparison of experimentally determined MMAD vs. CFD predicted NDSD. The dashed line represents a linear best fit to the data, which produced a correlation coefficient of $R^2$=0.88. The error bars represent +/- one standard deviation in the experimental results of MMAD. The NDSD parameter provides a good prediction of emitted aerosol size for the carrier-free formulation even though the devices employ different capsule chambers and the capsule have different vibrational frequencies and patterns of motion.

FIG. 7 provides a qualitative comparison of experimentally determined MMAD values vs. CFD predictions of the NDSD parameter. A linear fit of the data with an $R^2 = 0.88$ indicates a strong quantitative correlation. Therefore, the NDSD parameter is established as an effective means to predict the deaggregation of carrier-free powders. Considering all values of NDSD and performance in this study and Examples 2-4, a value of approximately 150 and above appears optimal for high efficiency aerosol generation. Existing inhalers produce NDSD values below 150 when operated at standard operating pressure drops of 4 kPa.

TABLE 7

Aerosolization performance and drug deposition (n = 3; Mean ± standard deviation) based on in vitro experiments of high efficiency inhalers with 3D metal rod arrays and without PTFE surface coating at a flow rate of 45-50 LPM.

| Description | $CC_1$-3D | $CC_L$-3D | $CC_A$-3D |
|---|---|---|---|
| Capsule retention (%) | 10.8 ± 1.0 | 8.6 ± 0.9 | 9.0 ± 0.6 |
| Flow passage retention (%) | 17.1 ± 2.2 | 11.6 ± 1.3 | 9.9 ± 1.0 |
| CC retention (%) | 7.0 ± 1.5 | 6.5 ± 3.1 | 5.5 ± 1.1 |
| Emitted (%) | 65.0 ± 4.1 | 73.4 ± 4.1 | 75.7 ± 0.4 |
| $FPF_{<5\ \mu m/ED}$ (%) | 91.4 ± 1.4 | 95.1 ± 0.2 | 94.3 ± 0.6 |
| $FPF_{<1\ \mu m/ED}$ (%) | 29.2 ± 0.2 | 31.4 ± 0.1 | 28.3 ± 0.8 |
| MMAD (µm) | 1.52 ± 0.01 | 1.49 ± 0.00 | 1.57 ± 0.02 |
| NDSD | 173.6 | 178.3 | 171.4 |

Example 9

Visual Feedback with the CCL-3D Inhaler During Correct Inhalation

When using DPIs, inhalation at a correct flow rate is important to properly aerosolize the drug powder and emit the full dose. An advantage of the $CC_L$-3D inhaler is that the capsule chamber is positioned within sight of the patient using the device. Due to negative pressure at the top of the capsule chamber during operation, the capsule rises during use to a height that is proportional to the inhalation flow rate. A clear or transparent window is included for viewing the capsule height along with markings of either flow rate, minimum operating flow rate, and/or optimal flow rate. In the device shown in FIGS. 5a and 5b, a red line is used to indicate the height that the top of the capsule should reach during optimal inhalation flow, which is 45-50 LPM for the current inhaler design, and may be higher or lower for other designs and different patient populations. FIG. 5a illustrates the $CC_1$-3D inhaler with a loaded capsule and no flow. FIG. 5b illustrates the inhaler with the correct 45-50 LPM of flow, which elevates the capsule to the red line, providing feedback that the correct inhalation rate is achieved.

Example 10

Use of an External Airflow Source with the 3D Rod Array

The 3D rod array dispersion unit was used to form an aerosol using an external flow source. The setup consisted of an approximately 1 L manual ventilation bag, an inline capsule chamber with a 3.1 mm air inlet orifice, and the 3D rod array. The size of the orifice was selected to produce sufficient vibration of the capsule thereby insuring good emitted dose and deaggregation. Powder formulation and in vitro assessments of device retention, emitted dose, and aerosol quality were identical to Example 7 using a proprietary spray dried submicrometer drug powder formulation. The ventilation bag was emptied twice, which would occur during two sequential patient inhalations when the device is used in practice. Separate experiments were conducted where the capsule was a standard HPMC capsule or coated with a low surface energy material. In vitro experimental results are shown in Table 8. Using the 3D array, a MMAD of less than 1.5 µm was achieved in both cases. Furthermore, both cases achieved $FPF_{5\ \mu m/ED}$ of approximately 80%. Use of PTFE coating improved emitted dose from approximately 70 to 80%.

TABLE 8

Aerosolization performance and drug deposition (n = 3;
Mean ± standard deviation) based on in vitro experiments
of an aerosol generation device employing the 3D rod array
and an external flow source with standard HPMC capsules and
low surface energy coated capsules. The inlet orifice was 3.1 mm.

| Description | 3D Rod Array No PTFE coating | 3D Rod Array With PTFE coating |
|---|---|---|
| Capsule retention (%) | 8.0 ± 1.0 | 6.4 ± 1.2 |
| Flow passage retention (%) | 9.2 ± 0.5 | 6.0 ± 0.6 |
| CC retention (%) | 7.1 ± 1.1 | 4.9 ± 1.3 |
| Connective tubing (%) | 3.6 ± 0.4 | 4.5 ± 0.3 |
| Emitted (%) | 72.0 ± 2.5 | 78.2 ± 0.9 |
| $FPF_{<5\ \mu m/ED}$ (%) | 77.6 ± 8.3 | 78.9 ± 5.8 |
| $FPF_{<1\ \mu m/ED}$ (%) | 26.1 ± 5.4 | 25.8 ± 3.8 |
| MMAD (μm) | 1.48 ± 0.11 | 1.47 ± 0.07 |

Example 11

Depositional Losses of High Fine Particle Fraction Aerosols in the Extrathoracic Airways With the use of aerosols having a high fine particle fraction, unwanted depositional losses in the extrathoracic airways can be minimized. The extrathoracic airways may include the mouth and throat (MT) for orally inhaled products or the nasal cavity and throat for nose-to-lung delivery. Commercial DPIs produce 30-90% depositional loss in the extrathoracic airways resulting in low and highly variable lung delivery efficiency (Borgstrom et al., 2006; Islam and Cleary 2012; Newman and Busse 2002; Weers et al., 2010). With the DPIs disclosed in this invention, the target MT depositional loss is less than 10% and may be as low as 5% or less when utilized with an optimized submicrometer combination drug powder formulation.

Mouth-throat depositional loss was evaluated at a standard inhaler pressure drop (4 kPa) and flow rate (45-50 LPM) for the $CC_1$-3D and $CC_L$-3D inhalers. Both inhalers employed metal rods in the 3D array without capsule coating. The powder formulation and in vitro assessment method for drug mass were previously described in Example 7 using a proprietary spray dried submicrometer powder formulation. The MT geometry was previously developed by Xi and Longest (2007) and shown to accurately represent dimensions of an average size adult male and capture mean MT deposition consistent with previous in vivo DPI studies (Delvadia et al., 2012a; Delvadia et al., 2012b). For the experimental setup, size characteristics of the aerosols were reported in Examples 7 and 8. Both inhalers produced an aerosol with a high fine particle fraction, with emitted dose ≥70%, $FPF_{5\ \mu m/ED}$≥90%, and MMAD ≤1.5 μm with a large submicrometer particle fraction ($FPF_{1\ \mu m/ED}$). The resulting depositional losses of the aerosols in the MT geometry was found to be <4.5% for each inhaler. This value represents an order of magnitude reduction in unwanted MT depositional loss compared with existing reported devices.

Example 12

Use of $CC_1$-3D and $CC_L$-3D with differing powder formulations

In this example, the aerosol performance of the two inhaler designs ($CC_1$-3D and $CC_L$-3D were compared using powder formulations containing different active ingredients. Table 9 shows the mean (SD) aerosol performance for a proprietary spray dried submicrometer powder formulation containing albuterol sulfate as the drug compound and compares it to a formulation containing terbutaline sulfate. Capsules were loaded with 2 mg of the respective powders and pierced with a 0.5 mm needle, placed in the inhalers, and actuated at a flow rate of 45-50 LPM. Drug dose remaining in the inhaler components, capsule, and emitted dose were determined with validated HPLC methods for albuterol sulfate or terbutaline sulfate, respectively. The drug aerosol was characterized using cascade impaction with a Next Generation Impactor and masses of drug on each stage were quantified using HPLC.

Table 9 shows that despite changing the active ingredient in the submicrometer powder formulation, for both inhalers, there was similar aerosol performance with respect to the drug device retention, emitted dose and aerosol dispersion characteristics. This suggests that the devices will be applicable to a range of drugs and not limited to the examples provided in this disclosure.

TABLE 9

Aerosolization performance and drug deposition (n =
3; Mean ± standard deviation) based on in vitro
experiments using albuterol sulfate and terbutaline sulfate formulations
in the $CC_1$-3D and $CC_L$-3D inhalers.

| Description | $CC_1$-3D Albuterol Sulfate | $CC_L$-3D Albuterol Sulfate | $CC_1$-3D Terbutaline Sulfate | $CC_L$-3D Terbutaline Sulfate |
|---|---|---|---|---|
| Capsule retention (%) | 10.8 ± 1.0 | 8.6 ± 0.9 | 11.5 ± 1.1 | 9.1 ± 1.6 |
| Flow passage retention (%) | 17.1 ± 2.2 | 11.6 ± 1.3 | 14.5 ± 1.7 | 10.6 ± 1.5 |
| CC retention (%) | 7.0 ± 1.5 | 6.5 ± 3.1 | 6.4 ± 0.3 | 5.6 ± 2.0 |
| Emitted (%) | 65.0 ± 4.1 | 73.4 ± 4.1 | 67.6 ± 2.0 | 74.6 ± 4.3 |
| $FPF_{<5\ \mu m/ED}$ (%) | 91.4 ± 1.4 | 95.1 ± 0.2 | 97.7 ± 0.4 | 96.7 ± 0.4 |
| $FPF_{<1\ \mu m/ED}$ (%) | 29.2 ± 0.2 | 31.4 ± 0.1 | 30.2 ± 2.6 | 28.9 ± 1.2 |
| MMAD (μm) | 1.52 ± 0.01 | 1.49 ± 0.00 | 1.49 ± 0.05 | 1.54 ± 0.03 |

Example 13

Figure 8:
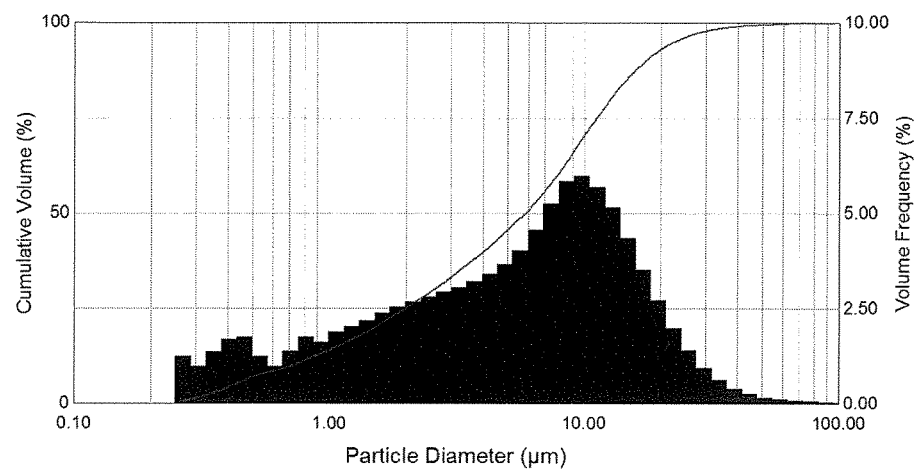
FIG. 8. Particle size distribution of budesonide powder formulation containing budesonide: sodium chloride:leucine (40:40:20% w/w) determined using the Malvern Spraytech.

Use of $CC_L$-3D with Conventional Micrometer Sized Budesonide Powder Formulation Previous examples demonstrated the performance of the invented inhalers using submicrometer powder formulations. It is also important to demonstrate that the present invention is also capable of aerosolizing conventional micrometer sized powder formulations. In this example, the $CC_L$-3D inhaler was employed to aerosolize a budesonide powder formulation. FIG. 8 shows the measured particle size distribution of the powder formulation.

FIG. 8 reveals that the powder has a mass median diameter of 5.5 μm. The aerosol performance of this formulation was tested using $CC_L$-3D, with and without PTFE capsule coating. Capsules were loaded with 2 mg of the powder and pierced with a 0.5 mm needle, placed in the inhalers, and actuated at a flow rate of 45 LPM. Drug dose remaining in the inhaler components, capsule, and emitted dose were determined with a validated HPLC method for budesonide. The aerosol was characterized using cascade impaction with a Next Generation Impactor and masses of drug on each stage were quantified using HPLC.

Figure 9:
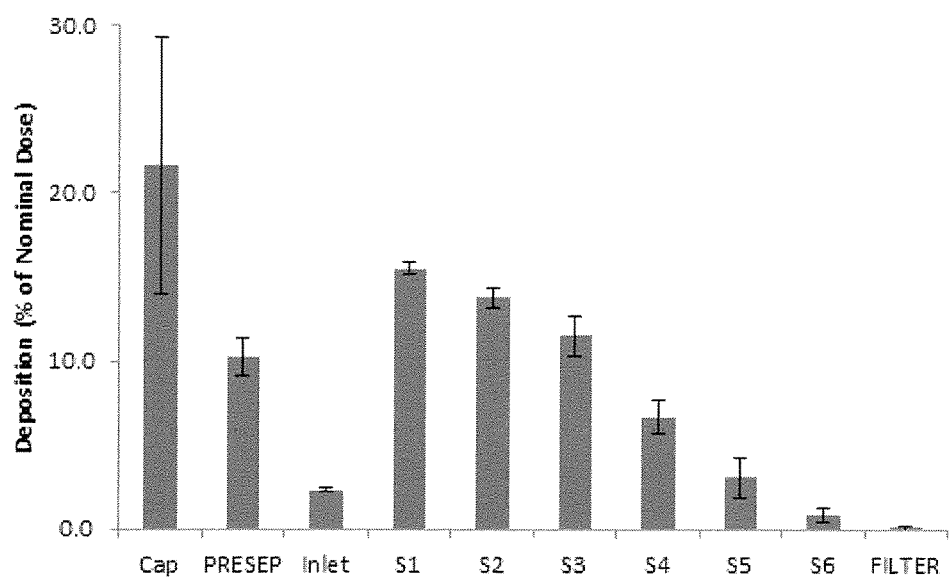
FIG. 9. Aerodynamic particle size distribution of budesonide from a micrometer sized powder formulation containing budesonide: sodium chloride:leucine (40:40:20% w/w) determined using the Next Generation Impactor and presented as fraction retained in the device and deposition on the stages of the impactor as a % of nominal dose.

FIG. 9 shows the aerodynamic particle size distribution for the micrometer size budesonide formulation when aerosolized using uncoated capsules with $CC_L$-3D in terms of drug retention in the device (capsule and base) and deposition on individual stages of the Next Generation Impactor (NGI). The mean (SD) emitted dose was 61.6 (4.3) % and the aerosol had an MMAD of 4.8 (0.1) μm.

Coating the capsule with PTFE had a significant effect on reducing the capsule retention of these micrometer sized particles and produced an increased emitted dose compared to the uncoated capsule. The mean emitted dose was 74.3% when coating was employed as shown in Table 10. This table also compares the aerosol performance of commercial budesonide formulations (Sahib et al., 2010) with the present invention. Perhaps most significant is the efficiency of aerosolization that is achieved with the $CC_L$-3D device; of the emitted dose, approximately 75% of the powder was dispersed as an aerosol <5 μm in size. The present invention achieves a higher emitted dose than both the nebulizer (Pulmicort Respules) and DPI (Turbuhaler) formulations. Although, the emitted dose is higher for the MDI formulation, the MDI aerosolization efficiency is poor, with only 25% of the ED that is less than 5 μm and available for inhalation. In contrast, the aerosol generated using the present invention, shows a high emitted dose (74.3%) combined with high aerosolization efficiency (FPF=74.9%). This indicates that the $CC_L$-3D inhaler is suitable for the aerosolization of conventional micrometer sized powders.

TABLE 10

Comparison of the aerosolization performance (n = 2-3; Mean ± standard deviation) based on in vitro experiments of commercial budesonide formulations (Sahib et al., 2010) with optimized inhaler $CC_L$-3D using coated capsules.

| Parameters | Pumicort Respules ® | Pulmicort Turbuhaler ® | Pulmicort Inhaler ® | $CC_L$-3D coated[f] |
|---|---|---|---|---|
| MMAD[a] | 4.48 ± 0.12 | 3.06 ± 0.03 | 3.38 ± 0.07 | 4.39 |
| GSD[b] | 2.00 ± 0.02 | 2.83 ± 0.12 | 2.25 ± 0.05 | 2.15 |
| ED[c] | 39.73 ± 0.52 | 52.94 ± 0.67 | 94.41 ± 0.35 | 74.3 |
| FPF[d] | 15.48 ± 0.61 | 28.44 ± 0.59 | 25.15 ± 1.18 | 74.9[e] |

Data represented as Mean ± SD, N = 3.
[a]Mass median aerodynamic diameter.
[b]Geometric standard deviation.
[c]Emitted dose.
[d]Fine particle fraction size < 3.9 μm.
[e]Fine particle fraction size < 5 μm.
[f]n = 2.

Example 14

Optimization of Spray Drying and Formulation Variable for Submicrometer Combination Particles Materials Albuterol sulfate, USP was purchased from Spectrum Chemical Co. (Gardena, Calif.). Pearlitol® PF-Mannitol was donated from Roquette Pharma (Lestrem, France). Poloxamer 188 (Leutrol F68) was donated from BASF Corporation (Florham Park, N.J.). Leucine and all other reagents were purchased from Sigma Chemical Co. (St. Louis, Mo.). Size 3 hydroxypropylmethyl cellulose (HPMC) capsules were donated from Capsugel (Peapack, N.J.). An Aerolizer® (Novartis; Basel, Switzerland) was obtained from a commercial pharmacy source. A Vortex® non-electrostatic holding chamber was purchased from PART Respiratory Equipment, Inc. (Midlothian, Va.). Molykote®316 silicone release spray was purchased from Dow Corning Corporation (Midland, Mich.).

Preparation of EEG Combination and Drug Only Dry Powder Formulations

Novel combination drug-excipient dry powder formulations were prepared using a Büchi Nano spray dryer B-90 (Büchi Laboratory-Techniques, Flawil, Switzerland). Albuterol sulfate (AS), mannitol (MN), L-leucine (Leu) and poloxamer 188 were selected as model drug, hygroscopic excipient, dispersion agent and surface active agent, respectively. To produce powder formulations which were readily dispersed upon aerosolization with a large portion of submicrometer particles, the spray drying and formulation variables were investigated during the optimization studies as shown in Table 11. The variables were drying chamber length, spray mesh size, inlet drying temperature, % leucine content, % ethanol concentration in the solvent, and % solids concentration. Each formulation contained 30% $^w/_w$ AS and 2% $^w/_w$ of poloxamer 188, based on the total solids concentration in the solutions. The following conditions were used during spray drying: the drying airflow was 120 L/min, the liquid feed rate was set to 100%, and the spray nozzle was a vibrating mesh.

As a control formulation, a drug only (D-AS) powder formulation, was also prepared by spray drying at the conditions applied to the optimized combination formulation. The dried solid particles were collected from the electrostatic precipitator in the spray drier and stored in sealed capped amber vials. The vials containing powders were stored in a desiccator (approx RH<10%) at room temperature.

AS drug content uniformity of the formulations was determined using a validated HPLC method. Briefly, a solution of each sample was prepared by dissolving approximately 3 mg of powder, which was accurately weighed, in 10 mL of deionized water. For the combination particles, this solution was then injected directing into the HPLC for quantification. For the drug only particles, the solution was further diluted to produce an AS concentration of approximately 100 μg/mL.

TABLE 11

Spray drying and formulation variables

| Expt | Dryer length (cm) | Inlet temp. (° C.) | Mesh size (μm) | Solids conc. (%, w/v) | Leucine (%, w/w) | Ethanol (%, v/v) |
|---|---|---|---|---|---|---|
| 1 | 45 | 85 | 4 | 1 | 20 | 20 |
| 2 | 90 | 85 | 4 | 1 | 20 | 20 |
| 3 | 90 | 70 | 4 | 1 | 20 | 20 |
| 4 | 90 | 70 | 5.5 | 1 | 20 | 20 |
| 5 | 90 | 70 | 4 | 0.2 | 20 | 20 |
| 6 | 90 | 70 | 4 | 0.5 | 20 | 20 |
| 7 | 90 | 70 | 4 | 0.5 | 20 | 0 |
| 8 | 90 | 70 | 4 | 0.5 | 10 | 20 |
| 9 | 90 | 70 | 4 | 0.5 | 0 | 20 |
| D-AS | 90 | 70 | 4 | 0.5 | N/A | 20 |

Aerodynamic Particle Size Characterization.

A Next Generation Impactor (NGI) (MSP Co., Shoreview, Minn.) was used to determine aerodynamic particle size characteristics of the drug in the combinations particle formulations. Each powder formulation (2 mg) was filled into size 3 HPMC capsules and placed into an Aerolizer® DPI prior to test. The capsule was fired into a NGI through a pre-separator operating at an air flow rate of 80 L/min for 3 seconds under at ambient conditions (25° C./45-55% RH). In order to assess the particle size distribution of the total dose of formulation, the USP induction port was omitted. The air flow rate of 80 L/min produced a pressure drop across the device of approximately 4 kPa. For each of the impactor experiments, the impactor collection stages and pre-separator were coated with a Molykore®316 silicone spray to minimize particle re-entrainment and bounce. Drug formulation remaining in the Aerolizer, deposited on the pre-separator, and on each of the impactor collections stages was extracted by washing each with 10 mL of deionized water for quantitative analysis. Collected samples were analyzed using a validated HPLC method.

Emitted dose (ED), defined as the percent of total loaded powder mass exiting the dry powder inhaler (DPI), was determined by subtracting the amount remaining in the DPI from the initial mass loaded into the DPI. The fine particle fraction ($FPF_{5\ \mu m/ED}$) and submicrometer particle fraction ($FPF_{1\ \mu m/ED}$), defined as the total emitted dose of particles with aerodynamic diameters smaller than 5 μm and 1 μm, respectively, were calculated via interpolation from the cumulative mass against the cutoff diameter of the respective stages of the NGI. Each measurement was repeated three times. The MMAD was determined at the $50^{th}$ percentile on the % cumulative undersize (probability scale) versus logarithmic aerodynamic diameter plot.

High-performance Liquid Chromatography (HPLC)

AS content in the combination and drug only formulations were analyzed using a validated HPLC method. A Waters 2690 separations module with a 2996 PDA detector (Waters Co., Milford, Mass.) was used. Chromatography was performed using a Restek Allure PFP 15×3 2 mm column (Bellefonte, Pa.). The mobile phase, consisting of methanol and ammonium formate buffer (20 mM, pH 3.4) in a ratio of 70:30, respectively, was eluted at a flow rate of 0.75 mL/min and the UV detector was set to a wavelength 276 nm. The column temperature was maintained at 25° C., and the volume of each sample injected was 50 μL.

Statistical Analysis

Data were expressed as the mean plus/minus standard deviation (SD). Statistical differences were studied by either analysis of variance or student's t-test using Jump 9.0 software (SAS Institute Inc., Cary, N.C.). P values of less than 0.05 were considered as statistically significant. To identify the statistically significant differences between formulation and spray drying variables, the aerosolization properties of the combination powder formulations were analyzed using one-way analysis of variance (one-way ANOVA) followed by post hoc Tukey-Kramer multiple comparisons test (Tukey HSD). The significance level was 0.05.

EEG Dry Powder Formulation Optimization

Combination drug-excipient powder formulations, consisting of an active pharmaceutical ingredient (API), a hygroscopic excipient, and a dispersion agent, were prepared using a Buchi Nano Spray Dryer for the EEG application. As shown in Table 11, a total of 9 spray-dried powders were investigated with the aim of optimization of the formulation and spray drying conditions to maximize the fraction of submicrometer particles in the DPI aerosol while maintaining a high emitted aerosol drug dose. Table 12 shows that all the combination particle formulations had similar % AS content and that they were close to the nominal value of 30% $^w/_w$.

Table 12 shows that, overall, the prepared combination particle formulations exhibited excellent aerosolization properties using the Aerolizer®. For these carrier free formulations, emitted doses (ED) were greater than 75% of the loaded dose and the fine particle fractions ($FPF_{5\ \mu m/ED}$) were greater than 80% of the emitted dose, for the formulations generated using a spray dryer equipped with the 90 cm drying chamber and the 4 μm spray mesh.

It was found that the aerosol characteristics of combination particle formulations were predominantly affected by the length of the drying chamber and the spray mesh size. For both these formulations, the submicrometer particle fractions ($FPF_{1\ \mu m/ED}$) were less than 5% and the MMAD was >3 μm (Table 12). The 90 cm drying chamber (Expt 2) was found to be better for generating individual, spherical particles than the 45 cm chamber (Expt 1). Thus, the 90 cm drying chamber and the 4 μm spray nozzle were used for all further studies. SEM images also suggested that the spray mesh size had the greatest influence on the primary particle size; a decrease in the spray mesh size (from 5.5 μm to 4 μm) significantly reduced the particle size (Expts 4 and 5, respectively).

TABLE 12

Effect of spray drying and formulation variables on the aerosolization characteristics of combination particles (values are means ± SD, n ≥ 3). Aerosols were produced using the commercially available Aerolizer DPI.

| Expt | ED (%) | MMAD (μm) | $FPF_{5\ \mu m/ED}$ (%) | $FPF_{1\ \mu m/ED}$ (%) |
|---|---|---|---|---|
| 1 | 82.1 (2.6) | 3.4 (0.2) | 66.2 (5.3) | 2.8 (0.6) |
| 2 | 78.3 (0.8) | 2.1 (0.1) | 91.5 (2.4) | 10.4 (2.2)* |
| 3 | 76.9 (0.2) | 1.8 (0.0) | 94.4 (0.5) | 14.5 (1.7) |
| 4 | 65.2 (1.2) | 3.3 (0.0) | 71.6 (0.8) | 4.7 (0.7)* |
| 5 | 84.2 (0.6) | 1.9 (0.3) | 81.4 (7.4) | 17.2 (6.0) |
| 6 | 81.4 (2.0) | 1.4 (0.1) | 95.3 (1.1) | 28.3 (3.1)# |
| 7 | 79.0 (0.7) | 1.7 (0.2) | 92.4 (4.5) | 17.6 (2.8)* |

*Statistically significant effect of the length of drying chamber, nozzle mesh size and ethanol amount on $FPF_{1\mu m/ED}$ (t-test: P < 0.05)
Statistical difference between solid concentrations, 0.2, 0.5 and 1%$_{w/v}$ (One-way ANOVA and post-hoc Tukey HSD: P < 0.05)

Decreasing the inlet drying temperature from 85° C. (Expt 2) to 70° C. (Expt 3) produced a small, but not significant, improvement in the dispersion characteristics of the DPI formulation. The solid concentration of spray solution was optimized at 0.5% $^w/_v$ (Expt 6) which provided the best aerodynamic performance among three concentrations, 0.2% $^w/_v$ (Expt 3), 0.5% $^w/_v$ and 1% $^w/_v$ (Expt 5); the $FPF_{1\ \mu m/ED}$ for the 0.5% $^w/_v$ formulation was almost double and MMAD decreased to 1.4 μm from 1.9 μm compared to the other solid concentrations. The incorporation of ethanol into the carrier solvent was observed to improve the aerosolization of powders (Table 12), although there is no noticeable change in the size and surface characteristics observed on SEM images between two formulations (Expts 6 and 7).

During the formulation development, it was observed that concentrations of greater than 20% $^w/_w$ leucine were required for solid particle formation during the spray drying process and to aid dispersion. The sprayed formulations with less than 20% $^w/_w$ leucine formed a thin film on the precipitator wall as the co-sprayed AS and MN formed a eutectic mixture.

The optimized condition for producing EEG combination particles was identified as Expt 6, and consisted of: 0.5% w/v solids concentration, consisting of AS, MN, Leucine and poloxamer 188 in a ratio of 30/48/20/2% $^w/_w$, respectively in a water:ethanol (80:20% $_{v/v}$) solution which was spray dried at 70° C. The submicrometer particle fraction ($FPF_{1\ \mu m/ED}$) of the optimized formulation (Expt 6) was 28.3% with an emitted dose of over 80%.

Example 15

Comparison of Characteristics of Novel Formulated Combination Particles and Unformulated AS Powder Scanning Electron Microscopy (SEM)

The morphology of the powders was observed using an EVO 50 SEM (Carl Zeiss AG, Germany). Each sample was mounted separately onto SEM stubs using double-sided copper tape and then coated with gold using a sputter coater (Electron Microscopy Sciences, Hatfield, Pa.) for 2 minutes under vacuum at 0.2 mbar. The SEM was operated at high vacuum with accelerating voltage 15 kV and specimen working distance 8 mm Thermal Analysis Thermograms were measured using a differential scanning calorimetry (DSC), Model 7 (Perkin Elmer Inc., Waltham, Mass.). Dry nitrogen gas was used as the purge gas through the DSC cell at a flow rate of 20 mL/min. Samples (3 mg) were weighed into aluminum crimped pinhole pans. The mass of the empty sample pan was matched with that of the empty reference pan within ±0.2 mg. Samples were heated at a rate of 10° C./min from 30 to 250° C. Thermogravimetric analysis (TGA) was conducted using a Pyris 1 system (Perkin Elmer Inc., Waltham, Mass.). Weight loss from 5 mg samples at a heating rate of 10° C./min from 30 to 250° C. under nitrogen purge (40 mL/min) was recorded.

Particle Size and Powder Density

Particle size distributions of the combination particles and the drug only particles were determined using a laser diffraction technique. This non-drug specific method assessed the particle geometric diameter based on volume fractions of the powders using a Spraytec® particle size analyzer equipped with an inhalation flow cell (Malvern Instruments, Ltd., Worcestershire, UK). The entire assembly operated in a closed system using the inhalation flow cell. Powders (approximately 2 mg) were filled into Size 3 HPMC capsules and loaded in to an Aerolizer® device. An airflow rate of 80 L/min was drawn through the system to sample the powder from the Aerolizer® and deliver the powder to the measurement zone. Skeletal density of the prepared powders was measured using an AccuPyc II 1340 gas phycnometer (Micrometritics Instrument Corporation, Norcross, Ga.) with a 1 cm³ volume capacity sample cup, and data was analyzed using V1.05 software. Theoretical estimates of aerodynamic diameter ($D_{ae}$) were derived from the Malvern determined volume median diameter ($D_{50}$) and the skeletal density (ρ), according to Eq. 1 (Edwards et al., 1997).

$$D_{ae} = D_{50} \times \sqrt{\frac{\rho}{\rho_1}}, \quad (4)$$

Where $\rho_1 = 1$ g cm⁻³

Formulated Combination and Unformulated AS Powder Characterization

Figure 10:
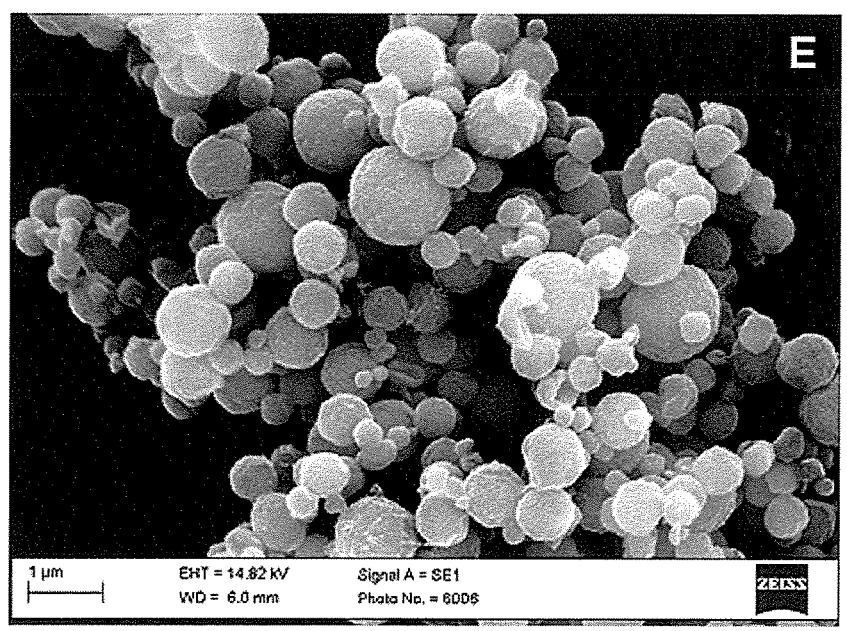
FIG. 10. SEM image of the prepared powder formulation: Expt 6.

The physico-chemical properties of the optimized combination formulation (Expt 6) were assessed. In order to investigate the importance of the combination particle excipients on the particle size and aerosol performance characteristics of the combination powder formulation, a drug only control formulation (D-AS) was produced using the same spray drying conditions however without excipients. FIG. 10 shows a SEM image of the optimized combination formulation. As an alternative particle size screening method to cascade impaction, Table 13 shows the particle size distribution characteristics for the optimized formulation (Expt 6) and the D-AS formulation determined using the Malvern Spraytec laser diffraction technique. The median particle size ($D_{50}$) of the combination formulation was 2.0 µm with a skeletal density of 1.33 g/cm³ (Table 13). The particle size data and density results were used to calculate a theoretical primary particle aerodynamic diameter ($D_{ae}$) of 2.3 µm, which appeared to be significantly greater than the MMAD (1.4 µm) determined by cascade impaction (Table 12). It is important to recognize there can be significant differences between drug specific cascade impaction studies and laser diffraction methods.

TABLE 13

Particle size distributions of the formulations, measured using a Spraytec® laser diffraction at an air flow rate of 80 L/min (values are means ± SD, n = 3)

| Samples | $D_{10}$ (µm) | $D_{50}$ (µm) | $D_{90}$ (µm) | $D_{ae}$ (µm) | $D_{ae}$/MMAD[1] |
|---|---|---|---|---|---|
| C-AS (R06) | 0.5 (0.0) | 2.0 (0.3) | 5.0 (0.5) | 2.3 | 1.6 |
| D-AS | 1.8 (1.5) | 29.2 (25.9) | 83.9 (53.9) | 33.3 | 17.5 |

[1]MMAD obtained impactor aerodynamic particle sizing experiments shown in Table 12

For the drug only formulation (D-AS), the particle size distribution appeared polydisperse with a median particle size ($D_{50}$) of 29.2 µm. This contrasts with the SEM image in FIG. 12f, which appears to show individual particles in the size range of 0.5 µm to 1.5 µm. In order to investigate this discrepancy, aerodynamic particle sizing using the NGI impactor was performed. For the D-AS formulation, poor deaggregation of the formulation was observed with only 30.9% of the formulation being deposited in the impactor for sizing, the remainder of the dose was deposited in the device and preseparator.

Figures 11A, 11B:
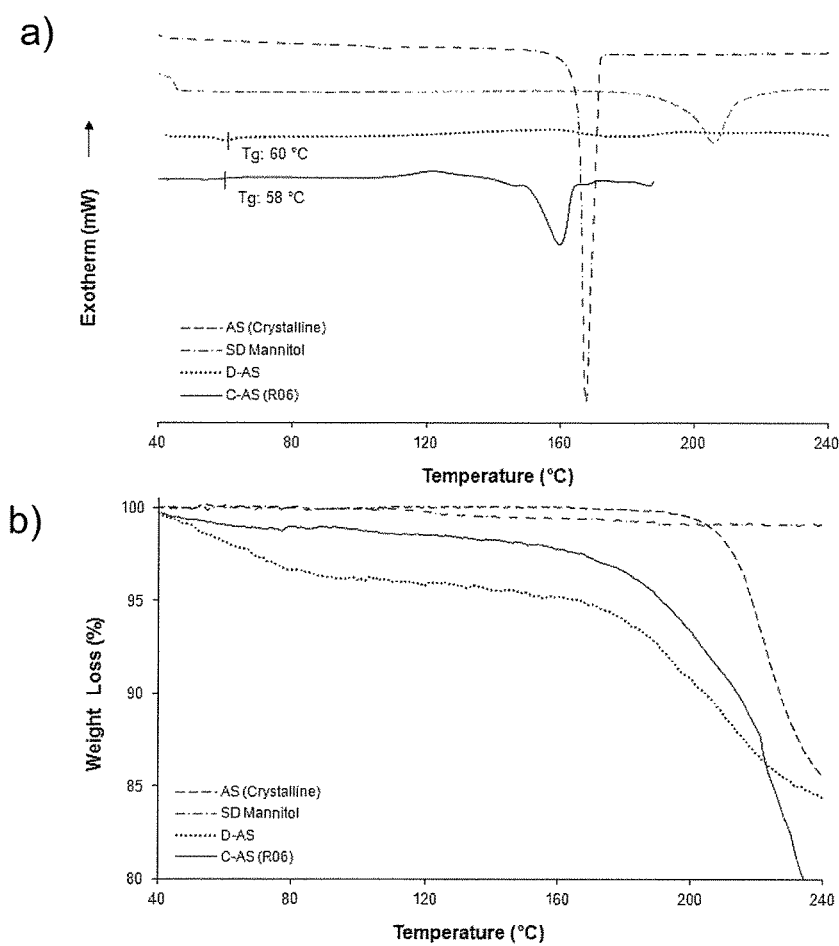
FIGS. 11a and 11b. DSC thermograms (a) and TGA results (b) for spray dried mannitol (SD Mannitol), crystalline AS, optimized C-AS (R06) and D-AS formulations.

Differential scanning calorimetry revealed that the albuterol sulfate in the combination formulation particles was present as an amorphous structure embedded in a crystalline MN matrix (FIG. 11a). A glass transition was observed at 58° C., corresponding to the glass transition of albuterol sulfate. The amorphous albuterol sulphate recrystallized at about 120° C. followed by decomposition at 180° C. Crystalline mannitol was observed to melt around 160° C. From the TGA analysis (FIG. 11b), the total weight loss for the combination formulation was 1.5% w/w upon drying.

The D-AS powders were also found to be amorphous. The DSC thermogram shows two endothermic processes associated with/without weight loss as seen in FIGS. 11a and 11b; the first one, at 60° C., corresponds to the glass transition temperature and the second one, at 160° C.-200° C., corresponds to decomposition of albuterol. TGA analysis of the D-AS formulation revealed the residual moisture content of 4.1% $^w/_w$.

Example 16

Aerosol Characterization in the Mouth-Throat (MT)-Tracheobronchial (TB) Model—Comparison of Novel Submicrometer Formulation (Expt 6) with Drug Only AS Particles (D-AS) and 3 µm Novel Formulated Combination Particles (Expt 4)

In Vitro MT-TB Model Deposition Study Using EEG Conditions

Figures 12A, 12B:
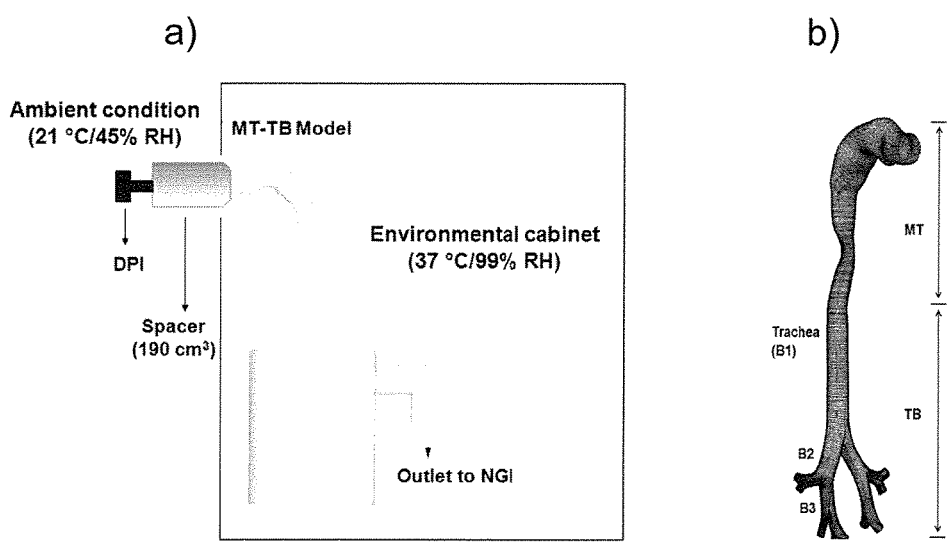
FIGS. 12a and 12b. (a) Schematic diagram of experimental setup for evaluating the growth of aerosols and (b) Detailed MT-TB geometry.

The MT deposition and hygroscopic growth of the optimized combination powder formulations and the drug only formulation were evaluated using in vitro deposition experiments in a MT-TB geometry. A schematic diagram of experimental set up for the EEG study is shown in FIG. 12a. The characteristic airway geometry consisted of a MT and upper TB section through the third respiratory bifurcation (FIG. 12b). The details of MT and upper TB components of this model were previously described in the studies of Tian et al. (Tian et al., 2011a; Tian et al., 2011b; Xi and Longest, 2007). The TB region of the model was housed in a chamber designed to provide a residence time of approximately one inhalation period (2 s) and route the aerosol into an impactor for sizing.

The MT-TB drug deposition and the final drug aerosol particle size exiting the model was assessed using EEG conditions (43° C./99% RH). To simulate the wet-walled conditions of the respiratory tract, the walls of the MT-TB model housed in the chamber were pre-wetted with humidified air (43° C./99% RH) for 30 minutes and the model was placed in an environmental cabinet (Espec; Hudsonville, Mich.) to maintain a wall temperature of approximately 37° C. The outlet of the model was connected either (i) a glass fiber filter when only MT deposition was being investigated or (ii) to the NGI via the spacer as shown in FIG. 12a which was also housed in the cabinet when the final drug particle size distribution following exposure to humidified conditions was being investigated. MT deposition and growth particle size results were compared to control experiments performed under ambient conditions at 25° C./45-55% RH. For all runs, the dry powder aerosol was generated using an Aerolizer®. Each powder formulation (1 mg) was filled into size 3 HPMC capsules and placed into an Aerolizer® prior to testing. The Aerolizer® was actuated using an air flow rate of 80 L/min for 3 seconds. Drug aerosol deposition in the MT and TB regions of the model and on each impactor stage were determined by washing each deposition site with 10 mL of deionized water. The collected samples were analyzed using a validated HPLC method.

Comparison of Novel Submicrometer Formulation (Expt 6) with Drug Only AS Particles (D-AS) and 3 µm Novel Formulated Combination Particles (Expt 4).

Figure 13:
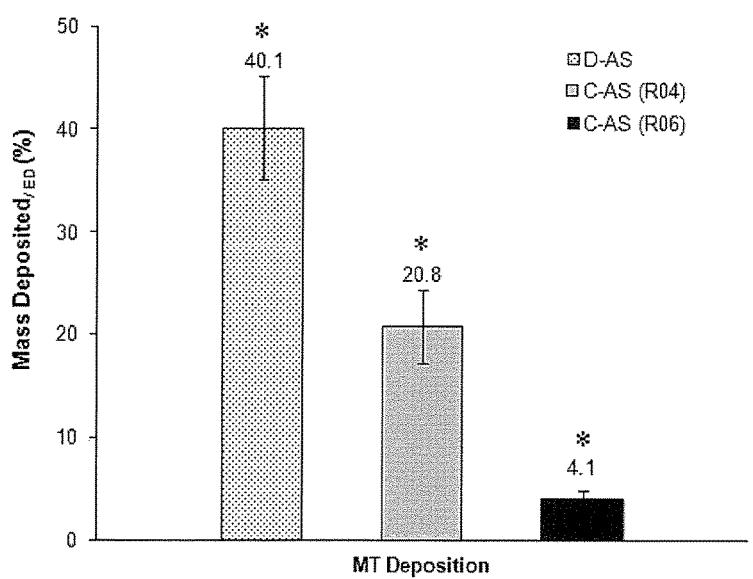
FIG. 13. Total deposition of the prepared formulations, drug only submicrometer AS particles (D-AS), 3 µm novel formulated combination particles (Expt 4) and optimized submicrometer formulated combination particles (Expt 6), emitted from a DPI (Aerolizer®) in the MT model (n≥4).

As shown in FIG. 13, overall, the novel combination formulation showed lower powder deposition in the MT region than the D-AS formulations at ambient conditions. The optimized combination powder (Expt 6) showed the lowest powder deposition as 4.1%, this is due to a combination of the submicrometer primary particles size and the excipients used in the combination particles. A formulated powder produced with a larger particle size (Expt 4) showed 20.8% powder deposition in MT region. The non-engineered D-AS powder demonstrated almost a ten-fold increase in the MT deposition that than the optimized powder formulation (Expt 6).

The behavior of the optimized powder formulation (Expt 6) in the MT-TB region was further studied with the MT-TB geometry using simulated respiratory environmental conditions. As shown in Table 14, there is no significant difference in the mass deposited in the MT between two test conditions, ambient (21/45-55% RH) and humidified conditions (37/99% RH), respectively. Based on the in vitro experiments with the MT-TB model, almost 95% of emitted particles successfully transited through the MT and upper TB region. The aerosolized dry powders from the Aerolizer® inhaler were characterized as having mean MMAD values of 1.6 µm at the MT inlet. Following passage through the humidified conditions in the MT-TB region, these aerosol particles had a final aerodynamic particle size of 3.2 µm. The initial submicrometer fraction ($FPF_{1\ \mu m/ED}$) of 20.7% decreased to 3% after exposure to the humidified conditions, indicating most submicrometer particles grew due to the hygroscopic nature of the mannitol excipient.

TABLE 14

The mean initial aerosol particle size and growth characteristics of the optimized C-AS (R06) formulation aerosolized using an Aerolizer ® at a flow rate of 80 L/min (n ≥ 4).

|  | Initial (21° C./45% RH) | Growth (37° C./99% RH) |
| --- | --- | --- |
| MMAD (µm) | 1.6 (0.1) | 3.2 (0.2)* |
| $FPF_{5\ \mu m/ED}$ (%) | 95.2 (1.3) | 72.8 (3.3)* |
| $FPF_{1\ \mu m/ED}$ (%) | 20.7 (1.1) | 3.0 (1.2)* |
| MT | 4.1 (0.7) | 3.4 (0.9) |
| TB | — | 2.0 (0.1) |

*Significant difference between two test conditions (t-test: P < 0.05)

Example 17

Preparation and Characterization of Novel Formulated Particles Using Alternate Hygroscopic Excipients Materials Sodium chloride and sodium citrate, respectively were investigated as alternative hygroscopic excipients to substitute for mannitol in the combination particle formulation. The methods for the production of the particles was as described previously using the Büchi Nano spray dryer B-90 (Büchi Laboratory-Techniques, Flawil, Switzerland). Novel combination drug-excipient dry powder formulations were prepared using albuterol sulfate (AS), L-leucine (Leu) and poloxamer 188 were selected as model drug, dispersion agent and surface active agent, respectively. Using the ratio obtained during the optimization process, mannitol (48% $^w/_w$), was replaced with either sodium chloride or sodium citrate, respectively. All other parameters remained as described in the optimization section.

Figures 14A, 14B, 14C:
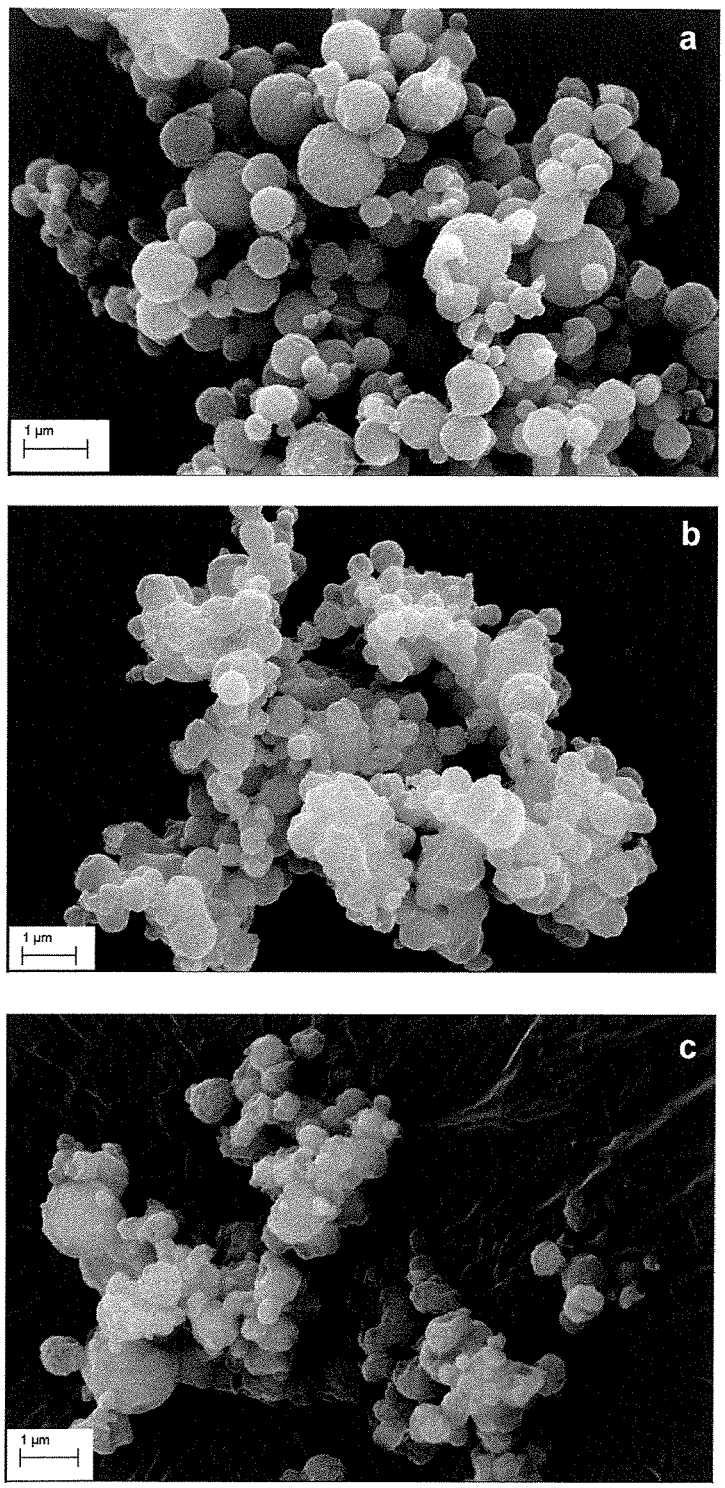
FIGS. 14a-14c. SEM images of the prepared powder formulations using: (a) Mannitol (AS-MN) (optimized, R06), (b) Sodium Citrate (AS-SC), (c) Sodium Chloride (AS-NC), as hygroscopic excipients. Overall, primary particles are shown to be smaller than 1 µm.

Characterization of Novel Formulated Particles Using Sodium Citrate and Sodium Chloride as Alternative Hygroscopic Excipients FIGS. 14a-14c compare the SEM images of formulated particles produced using (a) mannitol (AS-MN), (b) sodium citrate (AS-SC) and (c) sodium chloride (AS-NC) as hygroscopic excipients. FIGS. 14a-14c show that the primary particles were in submicrometer range, however, bridged particles appeared to be formed for the sodium citrate and sodium chloride formulations.

Tables 15 and 16 show that the aerodynamic properties of the powder were influenced by the properties of primary particles (initial size and presence of bridged particles) when aerosolized using the Aerolizer and modified Handihaler, respectively. Formulations containing salts were more hygroscopic than mannitol formulations; NaCl>sodium citrate>mannitol.

TABLE 15

Effect of hygroscopic excipient on the aerosolization characteristics of combination particles using the Aerolizer (values are means ± SD, n ≥ 3). Powder, 2 mg; Flow rate, 80 L/min for 3 s).

| Formulation | Powder collection | Impactor | MMAD (μm) | FPF 5 μm/ED (%) | FPF 1 μm/ED (%) |
|---|---|---|---|---|---|
| AS-MN | Ambient (<50% RH) | Ambient (<50% RH) | 1.4 (0.1) | 95.3 (1.1) | 28.3 (3.1) |
| AS-SC | <30% RH | Ambient (<50% RH) | 1.7 (0.1) | 93.5 (1.1) | 21.4 (1.7) |
| AC-NC | <20% RH | Ambient (<50% RH) | 2.1 (0.2) | 82.1 (2.7) | 15.5 (3.4) |

TABLE 16

Effect of hygroscopic excipient on the aerosolization characteristics of combination particles using the modified HandiHaler (values are means ± SD, n ≥ 3). Powder, 1 mg; Flow rate, 45 L/min for 5 s)

| Formulation | MMAD (μm) | GSD | Device retention (%) | $FPF_{5\ \mu m/ED}$ (%) | $FPF_{1\ \mu m/ED}$ (%) |
|---|---|---|---|---|---|
| AS-MN | 1.3 (0.1) | 2.0 (0.2) | 30.3 (0.6) | 96.0 (1.1) | 31.7 (1.6) |
| AS-SC | 1.4 (0.0) | 1.9 (0.0) | 28.4 (3.2) | 95.8 (0.6) | 29.1 (1.0) |
| AS-NC | 2.2 (0.0) | 2.6 (0.1) | 21.2 (4.1) | 68.2 (7.4) | 12.9 (3.5) |

REFERENCES

Behara, S. R. B., Farkas, D., Hindle, M., and Longest, P. W. (2013a) Development of a high efficiency dry powder inhaler: Effects of capsule chamber design and inhaler surface modifications. *Pharmaceutical Research*, (in review).

Behara, S. R. B., Frakas, D. R., Hindle, M., and Longest, P. W. (2013b) Development and comparison of new high efficiency dry powder inhalers for carrier-free formulations. *Journal of Pharmaceutical Sciences*, (in preparation).

Borgstrom, L., Olsson, B., and Thorsson, L. (2006) Degree of throat deposition can explain the variability in lung deposition of inhaled drugs. *Journal of Aerosol Medicine*, 19, 473-483.

Delvadia, R., Hindle, M., Longest, P. W., and Byron, P. R. (2012a) In vitro tests for aerosol deposition. II: IVIVCs for different dry powder inhalers in normal adults. *Journal of Aerosol Medicine and Pulmonary Drug Delivery*, DOI: 10.1089/jamp.2012.0975.

Delvadia, R., Longest, P. W., and Byron, P. R. (2012b) In vitro tests for aerosol deposition. I. Scaling a physical model of the upper airways to predict drug deposition variation in normal humans. *Journal of Aerosol Medicine*, 25(1), 32-40.

Edwards D. A., Hanes J., Caponetti G., Hrkach J., BenJebria A., Eskew M. L., Mintzes J., Deaver D., Lotan N., Langer R. (1997) Large porous particles for pulmonary drug delivery. Science 276:1868-1871.

Finlay, W. H. (2001) *The Mechanics of Inhaled Pharmaceutical Aerosols*, Academic Press, San Diego.

Geller, D. E., Weers, J., and Heuerding, S. (2011) Development of an inhaled dry-powder formulation of Tobramycin using PulmoSphere™ technology. *Journal of Aerosol Medicine and Pulmonary Drug Delivery*, 24(4), 175-182.

Hindle, M., and Longest, P. W. (2010) Evaluation of enhanced condensational growth (ECG) for controlled respiratory drug delivery in a mouth-throat and upper tracheobronchial model. *Pharmaceutical Research*, 27, 1800-1811.

Islam, N., and Cleary, M. J. (2012) Developing an efficient and reliable dry powder inhaler for pulmonary drug delivery—A review for multidisciplinary researchers. *Medical Engineering and Physics*, 34, 409-427.

Longest, P. W., Son, Y.-J., Holbrook, L. T., and Hindle, M. (2013) Aerodynamic factors responsible for the deaggregation of carrier-free drug powders to form micrometer and submicrometer aerosols. *Pharmaceutical Research*, DOI: 10.1007/s11095-013-1001-z.

Longest, P. W., Tian, G., Li, X., Son, Y.-J., and Hindle, M. (2012a) Performance of combination drug and hygroscopic excipient submicrometer particles from a softmist inhaler in a characteristic model of the airways. *Annals of Biomedical Engineering*, 40(12), 2596-2610.

Longest, P. W., Tian, G., Walenga, R. L., and Hindle, M. (2012b) Comparing MDI and DPI aerosol deposition using in vitro experiments and a new stochastic individual path (SIP) model of the conducting airways. *Pharmaceutical Research*, 29, 1670-1688.

Newman, S. (2009) *Respiratory Drug Delivery: Essential Theory and Practice*, RDD Online, Richmond.

Newman, S. P., and Busse, W. W. (2002) Evolution of dry powder inhaler design, formulation, and performance. *Respiratory Medicine*, 96, 293-304.

Sahib, M. N., Darwis, Y., Khiang, R. K., and Tan, Y. T. Z. (2010) Aerodynamic characterization of marketed inhaler dosage forms: High performance liquid chromatography assay method for the determination of budesonide. *African Journal of Pharmacy and Pharmacology*, 4, 878-884.

Son, Y.-J., Longest, P. W., and Hindle, M. (2012) Aerosolization characteristics of dry powder inhaler formulations for the enhanced excipient growth application: Effect of DPI design. *Respiratory Drug Delivery* 2012, 3, 903-906.

Son, Y.-J., Longest, P. W., and Hindle, M. (2013a) Aerosolization characteristics of dry powder inhaler formulations for the excipient enhanced growth (EEG) application: Effect of spray drying process conditions on aerosol performance. *International Journal of Pharmaceutics*, 443, 137-145.

Son, Y.-J., Longest, P. W., and Hindle, M. (2013b) Evaluation and modification of commercial dry powder inhalers for the aerosolization of submicrometer excipient enhanced growth (EEG) formulation. *European Journal of Pharmaceutical Sciences*. DOI: 10.1016/j.ejps.2013.04.011.

Tian G., Longest P. W., Su G., Hindle M. (2011a) Characterization of Respiratory Drug Delivery with Enhanced Condensational Growth using an Individual Path Model of the Entire Tracheobronchial Airways. *Annals of Biomedical Engineering* 39:1136-1153. DOI: 10.1007/s10439-010-0223-z.

Tian G., Longest P. W., Su G., Walenga R. L., Hindle M. (2011b) Development of a stochastic individual path (SIP) model for predicting the tracheobronchial deposition of pharmaceutical aerosols: Effects of transient inhalation and sampling the airways. *Journal of Aerosol Science* 42:781-799. DOI: 10.1016/j.jaerosci.2011.07.005.

Voss, A. P., and Finlay, W. H. (2002) Deagglomeration of dry powder pharmaceutical aerosols. *International Journal of Pharmaceutics*, 248, 39-40.

Weers, J. G., Bell, J., Chan, H. K., Cipolla, D., Dunbar, C., Hickey, A. J., and Smith, I. J. (2010) Pulmonary Formulations: What Remains to be Done? *Journal Of Aerosol Medicine And Pulmonary Drug Delivery,* 23, S5-S23.

Wilcox, D. C. (1998) *Turbulence Modeling for CFD, 2nd Ed.,* DCW Industries, Inc., California.

Xi, J., and Longest, P. W. (2007) Transport and deposition of micro-aerosols in realistic and simplified models of the oral airway. *Annals of Biomedical Engineering,* 35(4), 560-581.

Zisman, W. A. (1964) Relation of the Equilibrium contact angle to liquid and solid constitution. Advances in Chemistry, F. Fowkes, ed., American Chemical Society, Washington, D.C.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A drug delivery system for use with a dry powder for inhalation, comprising:
    a unit configured to hold or support the dry powder;
    an aerosol delivery port;
    a flow passage configured for air flow between said unit and said aerosol delivery port; and
    a three-dimensional rod array disposed in said flow passage comprising a plurality of rows, wherein each of said plurality of rows has a plurality of unidirectional rods, wherein said rows are spaced apart along a primary direction of air flow in said flow passage, and wherein the rods have a size in the range of 0.375 mm to 0.5 mm.

2. The drug delivery system as claimed in claim 1, wherein successive rows of said plurality of rows in said primary direction of air flow are staggered.

3. The drug delivery system as claimed in claim 1, wherein all the rods of said plurality of rows are oriented in a same direction.

4. The drug delivery system as claimed in claim 1, wherein said plurality of rods of each row of said plurality of rows have a uniform gap distance between said plurality of rods and wherein all of said plurality of rows are evenly spaced apart along said primary direction of air flow in said flow passage.

5. The drug delivery system as claimed in claim 1, wherein said unit is a capsule chamber configured to receive a capsule containing said dry powder.

6. The drug delivery system as claimed in claim 1, further comprising an external air source associated with said unit.

7. The drug delivery system as claimed in claim 1, wherein the rods have a circular, oval, square, or rectangular cross-section.

8. A dry powder inhaler (DPI) device, comprising:
    one or more air inlets;
    a capsule chamber associated with at least one of said one or more air inlets configured to receive a capsule containing a dry powder;
    an aerosol delivery port;
    a flow passage configured for air flow between said capsule chamber and said aerosol delivery port; and
    a three-dimensional rod array disposed in said flow passage comprising a plurality of rows, wherein each of said plurality of rows has a plurality of rods which are unidirectional, wherein said rows are spaced apart along a primary direction of air flow in said flow passage, and wherein the rods have a size in the range of 0.375 mm to 0.5 mm.

9. The device as claimed in claim 8, wherein successive rows of said plurality of rows in said primary direction of air flow are staggered.

10. The device as claimed in claim 8, wherein all the rods of said plurality of rows are oriented in a same direction.

11. The device as claimed in claim 8, wherein said plurality of rods of each row of said plurality of rows have a uniform gap distance between said plurality of rods and wherein all of said plurality of rows are evenly spaced apart along said primary direction of air flow in said flow passage.

12. The device as claimed in claim 8, further comprising an external air source associated with said one or more air inlets.

13. A dry powder inhaler (DPI) device, comprising:
    one or more air inlets;
    a capsule chamber associated with at least one of said one or more air inlets for receiving a capsule containing a dry powder; and
    an aerosol delivery port configured for the egress of air which has passed through said capsule chamber;
    wherein said capsule chamber is configured to orient a primary capsule axis of said capsule perpendicular to a primary direction of air flow in said capsule chamber and allow for vibratory motion of said capsule such that said capsule makes repetitive right angle impacts with one or more capsule chamber walls.

14. The device as claimed in claim 13, wherein said vibratory motion is in a plane which is perpendicular to said primary direction of air flow in said capsule chamber.

15. The device as claimed in claim 13, further comprising an external air source associated with said one or more air inlets.

16. A dry powder inhaler (DPI) device, comprising:
    one or more air inlets;
    a capsule chamber associated with at least one of said one or more air inlets and configured to receive a capsule containing a dry powder; and
    an aerosol delivery port configured for the egress of air which has passed through said capsule chamber;
    wherein said capsule chamber is configured at an inclined angle to a downstream flow path between said capsule chamber and said aerosol delivery port, and
    wherein said capsule chamber is configured to allow for vibratory motion of the capsule.

17. The device as claimed in claim 16, wherein said inclined angle is approximately 90°.

18. The device as claimed in claim 16, wherein said inclined angle is less than 90°.

19. The device as claimed in claim 16, further comprising an external air source associated with said one or more air inlets.

20. A dry powder inhaler (DPI) device, comprising:
    one or more air inlets;
    a chamber associated with at least one of said one or more air inlets and configured to receive a capsule containing a dry powder, the chamber being sized to permit a plurality of positions of said capsule within said chamber;
    an aerosol delivery port configured for the egress of air which has passed through said chamber; and
    an indicator associated with said chamber for indicating a position of said capsule within said chamber;
    wherein said one or more air inlets, said chamber, and said aerosol delivery port are configured such that said position of said capsule within said chamber is a function of inhalation flow rate.

21. The device as claimed in claim 20, wherein said indicator comprises a viewing window in a wall of said chamber for viewing said position of said capsule within said chamber.

22. The device as claimed in claim 21, wherein said viewing window is positioned in view of a user during inhalation.

23. The device as claimed in claim 20, wherein said indicator comprises indicia.

24. The device as claimed in claim 20, further comprising an external air source associated with said one or more air inlets.

25. The device as claimed in claim 20, wherein the chamber is configured to accommodate only one capsule at a time.

26. A drug delivery system for use with a dry powder, comprising:
- a capsule containing a dry powder, wherein said dry powder comprises one or more of a medicament, a hygroscopic excipient, a dispersion agent, and a surface active agent;
- a capsule chamber configured to receive said capsule;
- an aerosol delivery port;
- a flow passage configured for air flow between said capsule chamber and said aerosol delivery port; and
- a three-dimensional rod array disposed in said flow passage comprising a plurality of rows, wherein each of said plurality of rows has a plurality of unidirectional rods, wherein said rows are spaced apart along a primary direction of air flow in said flow passage, and wherein the rods have a size in the range of 0.375 mm to 0.5 mm.

* * * * *